(12) United States Patent
Darougar et al.

(10) Patent No.: US 6,264,971 B1
(45) Date of Patent: Jul. 24, 2001

(54) OCULAR INSERT

(75) Inventors: Sohrab Darougar, East Croydon; Dayshad Darougar, South Croydon, both of (GB)

(73) Assignee: BTG International Limited, London (GB)

(*) Notice: Subject to any disclaimer, the term of this patent is extended or adjusted under 35 U.S.C. 154(b) by 0 days.

(21) Appl. No.: 09/428,967

(22) Filed: Nov. 4, 1999

(51) Int. Cl.⁷ .................................................. A61F 9/00
(52) U.S. Cl. ........................................... 424/427; 424/428
(58) Field of Search ........................ 424/427, 428, 424/429, 422

(56) References Cited

U.S. PATENT DOCUMENTS

| | | | | |
|---|---|---|---|---|
| 3,416,530 | * | 12/1968 | Ness | 128/261 |
| 3,845,201 | * | 10/1974 | Haddad | 424/22 |
| 3,949,750 | | 4/1976 | Freeman | 128/260 |
| 4,135,514 | * | 1/1979 | Zaffaroni et al. | 128/260 |
| 4,179,497 | * | 12/1979 | Cohen et al. | 424/22 |
| 4,186,184 | * | 1/1980 | Zaffaroni | 424/14 |
| 4,343,787 | * | 8/1982 | Katz | 424/78 |
| 5,147,647 | | 9/1992 | Darougar | 424/427 |
| 5,322,691 | | 6/1994 | Darougar et al. | 424/427 |
| 5,395,618 | | 3/1995 | Darougar et al. | 424/427 |

FOREIGN PATENT DOCUMENTS

| | | |
|---|---|---|
| 92/00112 | 1/1992 | (WO) . |
| 95/01764 | 1/1995 | (WO) . |

* cited by examiner

*Primary Examiner*—Thurman K. Page
*Assistant Examiner*—Amy E. Pulliam
(74) *Attorney, Agent, or Firm*—Nixon & Vanderhye

(57) ABSTRACT

A flexible ocular insert device adapted for the controlled sustained release of a drug upon insertion into the upper or lower fornix of the eye. The device comprises an elongate body of a polymeric material including two end portions, wherein the body contains a pharmaceutically active ingredient, and wherein the device has a length of at least 8 mm and a maximum diameter not exceeding 1.9 mm. The device is sufficiently flexible to allow it to bend along the curvature of the eye within the upper or lower fornix upon its being positioned so that the longitudinal axis of the device is generally parallel to the transverse diameter of the eyeball, and the device does not extend onto any visible portion of the eyeball. Each of the end portions of the device is tapered towards the extremities of the device.

32 Claims, 15 Drawing Sheets

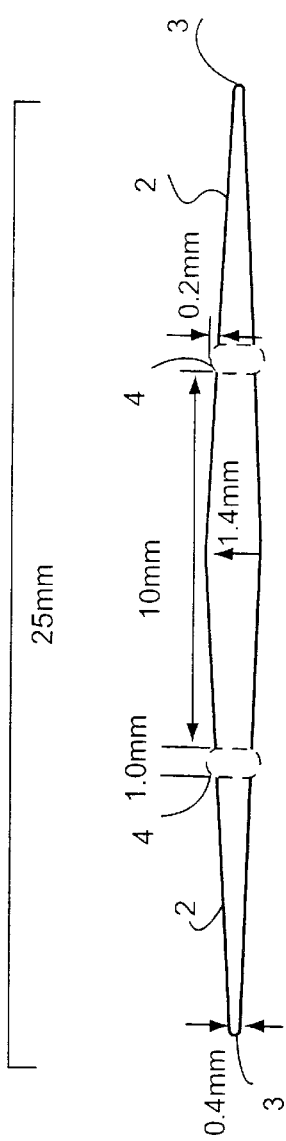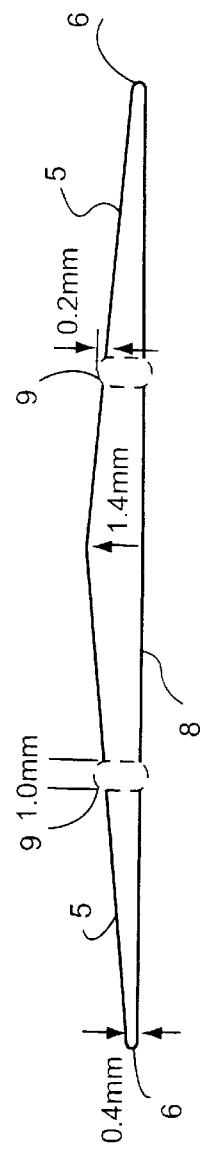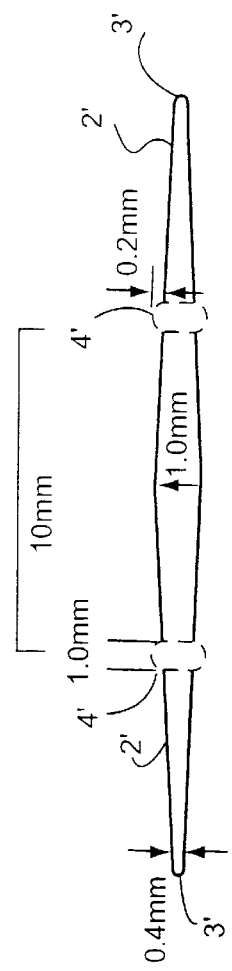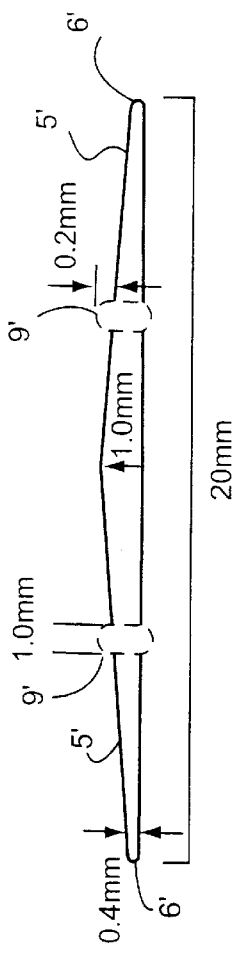

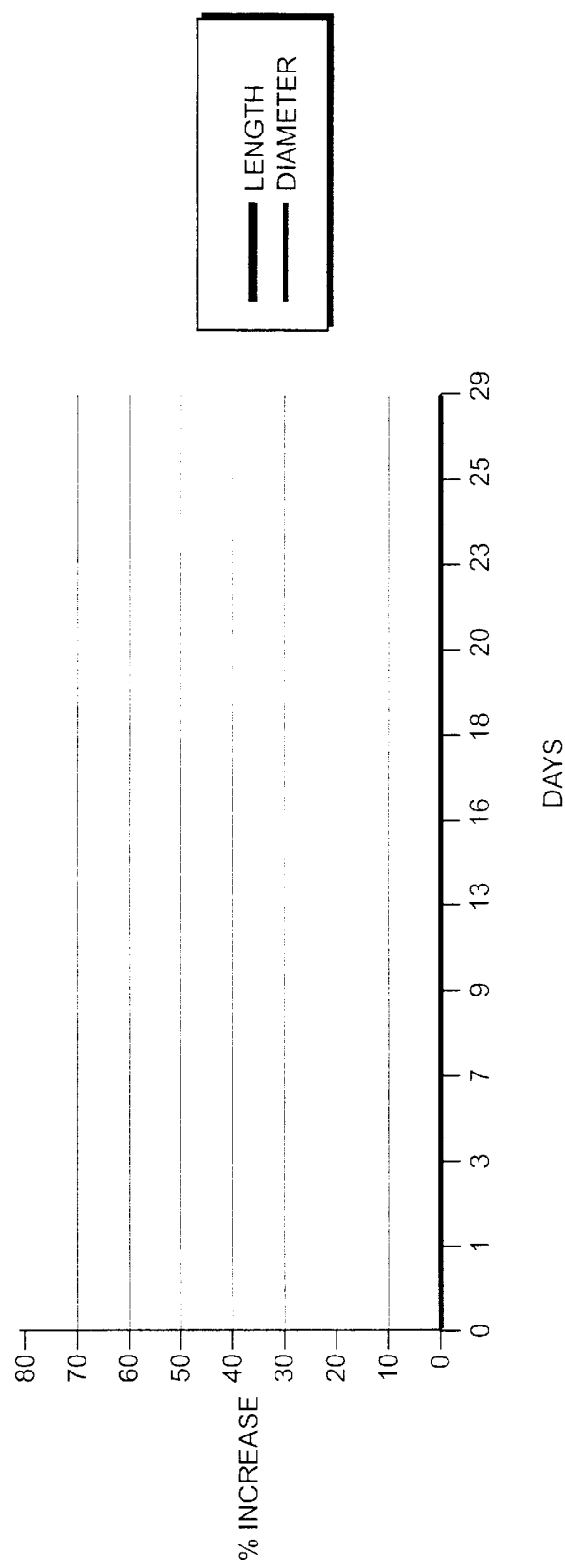
Fig. 18  INCREASE IN THE LENGTH AND DIAMETER OF PLAIN SDRD-3 SOAKED IN WATER

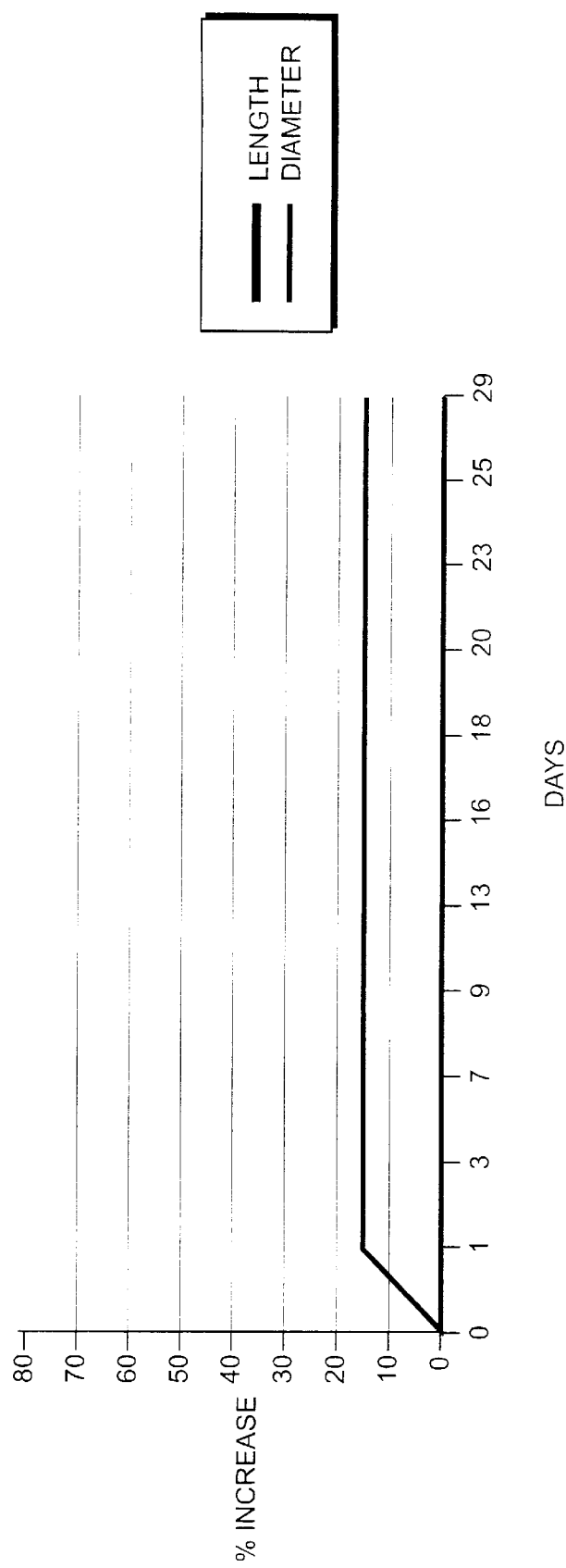
Fig. 19 INCREASE IN THE LENGTH AND DIAMETER OF SDRD-3 CONTAINING CARBOPOL 5% SOAKED IN WATER

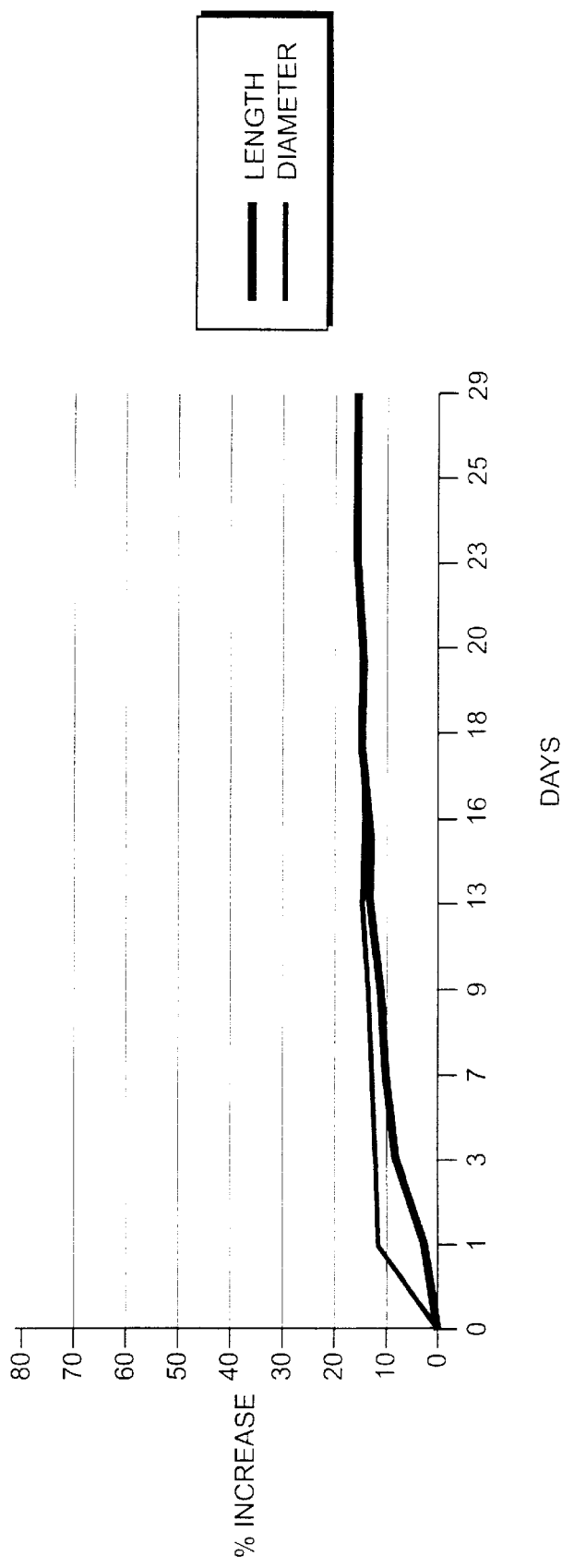
Fig. 20  INCREASE IN THE LENGTH AND DIAMETER OF SDRD-3 CONTAINING HPMC 20% SOAKED IN WATER

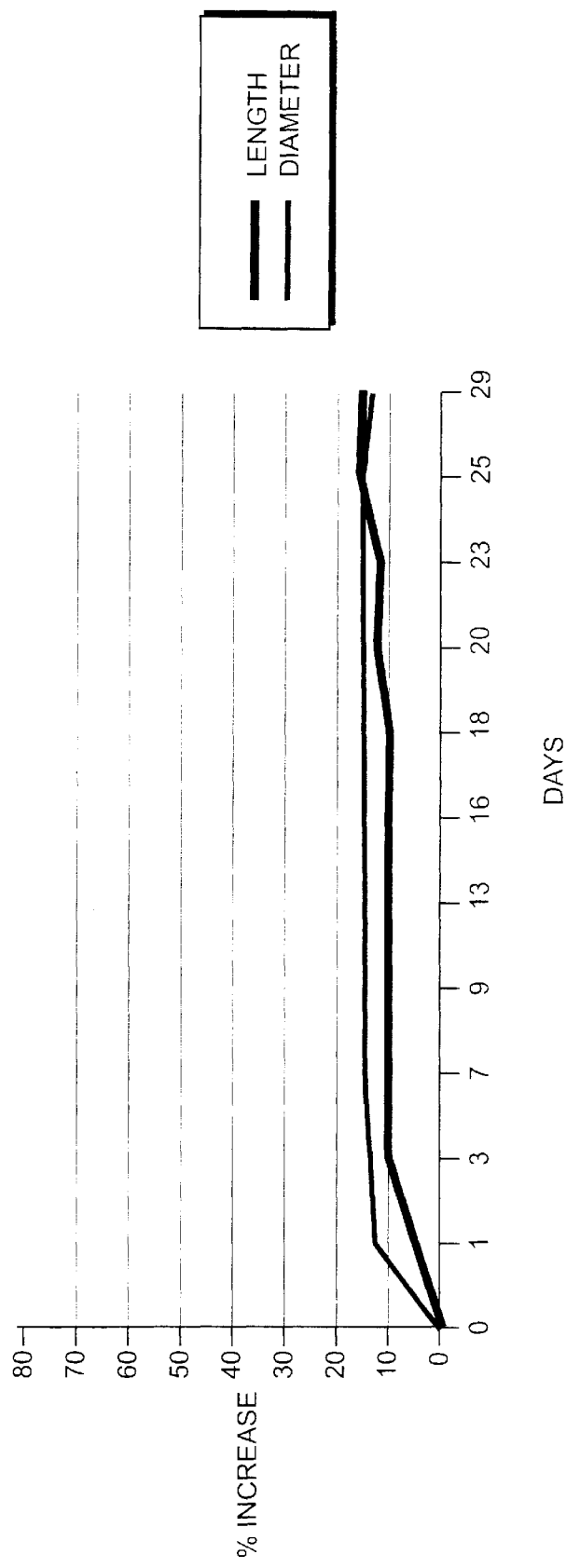
Fig.21 INCREASE IN THE LENGTH AND DIAMETER OF SDRD-3 CONTAINING CABOPOL 5% AND HPMC 20% SOAKED IN WATER

OCULAR INSERT

TECHNICAL FIELD

This invention is concerned with improvements in or relating to ocular insert devices.

BACKGROUND ART

Various diseases of the eye are commonly treated by frequent daily application of ophthalmic drugs for example in the form of eye drops or ointment. While this is suitable and convenient in some cases, it can be a serious disadvantage that the drug is not present in the eye in a continuous manner. With a view to overcoming this disadvantage it has been previously proposed, for example, in U.S. Pat. No. 3,416,530 of R. A. Ness assigned to Alza Corporation and subsequent patents of Alza Corporation to provide a flexible ocular insert device adapted for the controlled sustained release of the drug.

In for example U.S. Pat. No. 3,828,777 of R. A. Ness assigned to Alza Corporation it is stated that the ocular insert can be fabricated in any convenient shape for comfortable retention in the conjunctival sac of the eye and that the marginal outline can be ellipsoid, doughnut-shape, bean-shape, banana-shape, circular or rectangular; and in cross section it can be doubly convex, concavoconvex, or rectangular. It is suggested however that the original cross-sectional shape of the device is not of controlling importance. However, these previously proposed devices have in practice met with no more than limited success because most of the proposed shapes and sizes were not suitable for placement in the narrow upper and lower fornices. Also, previous devices have tended not to remain in place in the eye and have at times caused irritation to the patient during use.

U.S. Pat. No. 4,186,184 to A. Zaffaroni discloses that the length of an insert device should be from 2 to 20 mm, its width 1 to 15 mm and its thickness 0.1 to 4 mm. A wide variety of shapes are disclosed including ellipsoid, doughnut, bean, banana and square shapes.

U.S. Pat. No. 3,828,777 to Ness discloses an ocular device which is inserted in that portion of the eye bounded by the surfaces of the bulbar conjunctiva of the sclera of the eyeball and the palpebral conjunctiva of the lid. Such placement of the device would, however, be subject to eye movement and would not provide an anchored position such as is obtained in the present invention. Movement of the device causes pain, irritation, foreign body sensation and watering.

U.S. Pat. No. 4,343,787 to Katz discloses water soluble inserts for the eye in which broad dimensional ranges of sizes and shapes are employed. There is no description of an insert of a specific size and shape to allow it to be retained in the fornix portion of the eye.

U.S. Pat. No. 4,135,514 to Zaffaroni et al. relates to osmotic drug delivery devices which can be used for the administration of ocular drugs. A wide variety of shapes and sizes is disclosed.

EP-A-0 033 042 to Merck and Co., Inc. discloses ocular inserts which can take any of a variety of shapes, one of which may be an extruded rod. There is no description, however, of a device having dimensions which make it suitable for insertion into the fornix so as to be retained therein for 7 days or longer.

U.S. Pat. No. 4,730,013 to Bondi et al. discloses ocular inserts intended to overcome the problem of blurred vision arising from the use of particular insert materials. The maximum length of 5 mm employed by Bondi et al. is considerably smaller than the range of dimensions employed in the present invention. It is disclosed in this patent that a device with a length of 5 mm falls well below the minimum length required for retention in the eye of humans for 7 days or more.

EPO 0 251 680 to IOLAB, Inc. discloses a device for controlled drug release to the eye, in which an external matrix rapidly soluble in body fluids and having bioerodible microparticles containing the drug are positioned in the upper or lower conjunctival cul-de-sac of the eye. There is no description of a device which is retained in the eye for seven days or longer, or of the specific shape and dimension of the device of the invention for placement in the upper or lower fornix.

U.S. Pat. No. 3,845,201 to Haddad et al. discloses an ocular device for insertion in the cul-de-sac of the conjunctiva. The device may be any of various shapes, preferably disc shaped.

U.S. Pat. No. 4,164,559 to Miyata et al. discloses soluble device for drug delivery to the eye including collagen insert having an ovoid shape. The device is described as insertable into the inferior fornix. There is no description of a device having the dimensions employed in the present invention for retention of seven days or longer.

U.S. Pat. No. 4,179,497 to Cohen et al. discloses water soluble inserts of various shapes for applying drugs to the cul-de-sac of the conjunctiva. Again there is no description of an insert having the specific dimensions of the invention.

In the use of a prior art device known as Ocusert, the subject of U.S. Pat. No. 3,828,777 to Ness, the device is inserted into the conjunctival cul-de-sac. Either of two systems may be employed, with the Pilo-20 system measuring 5.7×13.4 mm on its axes and 0.3 mm in thickness and the Pilo-40 system measuring 5.5×13 mm on its axes and 0.5 mm in thickness. Various problems in retention and irritation which occurred in the use of this device are documented, for example, in the following publications: P. Sihvola et al., Practical problems in the use of Ocusert-pilocarpine delivery system, *Acta Ohthalmol.* (Covenh.), December 1980, 58 (6), pp 933–937; S. E. Smith et al., Comparison of the pupillary, retractive and hypotensive effects of Ocusert-40 and pilocarpine eyedrops in the treatment of chronic simple glaucoma, *Br. J. Oohthalmol.*, April 1979, 63(4) pp 228–232; and I. P. Pollack et al., The Ocusert pilocarpine system: advantages and disadvantages, *South Med. J.*, October 1976, 69 (10), pp 1296–1298.

Other ocular inserts are described in the following literature reports: Urtti et al. (1990) Controlled drug delivery devices for experimental ocular studies with timolol.1.In vitro release studies. *Int. J. Pharm.*, 61, 235–240; and Urtti et al (1990) Controlled drug delivery devices for experimental ocular studies with timolol.2.Ocular and systemic absorption in rabbits. *Int. J. Pharm.*, 61, 241–249. These reports describe the use of a permeable hollow tube (silicone) for ocular delivery. The tube has a diameter of 1.94 mm which is outside the dimensions employed in the present invention. Also, the device was only observed in the eye for an 8 hour period.

EP-A-0,262,893 discloses a flexible ocular insert device adapted for the controlled sustained release of an ophthalmic drug into the eye, which comprises a body having a thin elongated circular cylindrical configuration, the device having for example a length of at least 8 mm and a diameter not exceeding 1 mm. The circular cylindrical body terminates at transverse end surfaces which may for example be planar or domed.

Previously published U.S. Pat. No. 5,395,618 discloses a flexible ocular insert device adapted for the controlled sustained release of an ophthalmic drug upon insertion into the upper or lower fornix of the eye, said device comprising an elongated body of a polymeric material in the form of a rod or tube containing a pharmaceutically active ingredient and with at least two anchoring protrusions extending radially outwardly from said body, said device having a length of at least 8 mm and a diameter including protrusions not exceeding 1.9 mm, wherein said device is sufficiently flexible to allow it to bend along the curvature of the eye within the upper or lower fornix upon being positioned so that the longitudinal axis of said device is generally parallel to the transverse diameter of the eyeball, said device being of a size and configuration such that, upon insertion into the upper or lower fornix, the device does not extend onto any visible portion of the eyeball, said device being independent of movement of the eye and remaining out of the field of vision so as to be well retained in place and imperceptible by the patient over a prolonged period of use, said protrusions acting to minimise lateral movement of the device within the fornix, whereby the device when inserted into the upper or lower fornix can be retained therein for more than seven days.

However, their retention is sub-optimal as far as comfort, adverse effects, movement within the fornix felt by the patient, foreign body sensation and irritation in general.

SUMMARY OF THE INVENTION

The present invention in a first aspect provides a flexible ocular insert device adapted for the controlled sustained release of a drug upon insertion into the upper or lower fornix of the eye, said device comprising an elongate body of a polymeric material including two end portions said body containing a pharmaceutically active ingredient, said device having a length of at least 8 mm and a maximum diameter not exceeding 1.9 mm, wherein said device is sufficiently flexible to allow it to bend along the curvature of the eye within the upper or lower fornix upon being positioned so that the longitudinal axis of said device is generally parallel to the transverse diameter of the eyeball, said device being of a size and configuration such that, upon insertion into the upper or lower fornix the device does not extend onto any visible portion of the eyeball, and in which each of said end portions is tapered towards the extremities of the device.

It has been found that such a flexible ocular insert device, is well retained in place and tolerated better by the patient over a period of use more prolonged than hitherto possible.

Whereas the flexible ocular insert device of U.S. Pat. No. 5,395,618 permitted use of up to 7 or 14 days or longer in the upper fornix but usually less than 2 days in the lower fornix. Only between 14 to 47% of patients could retain the device in the upper fornix for 28 days or longer. The flexible ocular insert device of the present invention has been found to be retained by 72% of people for 28 days or longer when in the upper fornix and was retained in 36% of people for 28 days or longer when in the lower fornix.

The increased retention of the device fitted in the upper fornix means the device can be used to deliver drugs to the eyes to treat ailments requiring long term continuous treatment, ie one application for the treatment or prevention of infection or allergy or application every 1 to 3 months or longer for chronic diseases. The fact that the device may be fitted and removed by the patients themselves into and out of the upper or lower fornix which, coupled with the high retention period in the fornices now allows the patient to fit a device of the present invention for self application of treatments that would previously have required an experienced person to fit and remove an ocular device to and from the fornices of a patient.

The device is designed to be inserted in the conjunctival folds of the upper or lower fornix at the junction between the palpebral conjunctiva of the upper or lower eyelid and bulbar conjunctiva of the eyeball, being held in position preferably in the extreme outer and inner end portions of the upper or lower fornix and prevented from moving downward or laterally respectively by the pressure and movement of the lid against the eyeball. The tapered end portions, at least in part, lie between the upper or lower tarsus and the eyeball, because they are conical, they serve to prevent the device moving laterally in the fornix whilst also providing a reduced pressure on the eyeball compared to known prior art inserts when similarly positioned in the eyes, thereby providing increased comfort and tolerability for the patient.

The device may include optional radial protrusions acting, in use, to minimise lateral movement of device within the fornix, preferably two protrusions each positioned to lie adjacent the tarsus, in use.

The device may have protrusions extending outwardly a distance such that the overall diameter of the device including the protrusions is approximately 15 to 30% greater than the diameter of the body of said device. They may, for example, be positioned so as to be symmetrical disposed about the centre point of said body.

The protrusions, if present, are preferably toroidal or doughnut shaped around the body to provide a ribbed configuration.

The body of device may include a cylindrical portion between the two end portions or be entirely formed by the two end portions, the end portions having a common base. The tapered end portions may each be in the form of a right circular cone or an oblique circular cone. Preferably, the apex of each end portion is rounded.

The length of the device is conveniently from 8 to 25 mm for use in the lower fornix to suit the eyes of different sizes such as infants, children and adults, or from 8 to 35 mm for use in the upper fornix to suit the eyes of different sizes such as infants, children and adults.

The diameter of individual devices including protrusions is preferably from 0.5 to 1.9 mm to suit the eyes of different sizes such as infants, children and adults.

The mechanism of drug release may be, for example, by diffusion through an outer wall of the device, osmosis, bioerosion, or diffusion including possible drug dissolution.

The polymeric material of the device may be, for example, a silicone elastomer, made of hydrogel components or be a methacrylate or hydroxymethacrylate based material.

In particular, the device is advantageously inserted so as to fit within the upper or lower fornix by restriction of the cross sectional dimensions of the device to allow it to slip into this position and then with a length that provides for anchoring the device across the fornix. Two or more protrusion elements, when present, extend radially outwardly from the core to minimize lateral movement when the device is positioned within the fornix. By locating the device within the fornix, the device is imperceptible to the patient, through restriction of the device to a specific size range and shape, with the upper limit not being governed by the geometric space limitation of the whole eye, and by placement specifically within the fornix, not simply within the conjunctival cul-de-sac. In addition, the retention of the present insert device is independent of the movement of the eye or the lid by virtue of the fornix anatomy. In contrast, a device placed anywhere on the bulbar conjunctiva would be subject to eye and or lid movement and cause discomfort to the patient.

The insert device of the present invention must be positioned precisely and remain anchored in the upper or lower fornix, known also as the superior conjunctival fornix or the inferior conjunctival fornix, as distinct from the positioning of other kinds of devices anywhere in the conjunctival cul-de-sac. The device of the present invention must be flexible to allow it to bend along the curvature of the eye within the fornix. In particular, such flexibility must be sufficient to allow it to bend in the upper or lower fornix upon being positioned so that the longitudinal axis of the device is generally parallel to the transverse diameter of the eyeball.

The present insert device is imperceptible by the patient when anchored properly in the fornix, whereas prior art devices are perceived as foreign bodies. Upon proper positioning in the fornix, the present insert device is independent of eye or lid movement and does not move when the eye or lid moves. The conical end portions improve retention in the required position whilst at the same time reducing adverse effects so leading to improved retention characteristics. The device of the present invention also retains out of the field of vision. In addition, it can be placed and held in position without interference during surgical procedures.

The length of the present insert device is also critical to the anchoring process in the fornix. The length of the device is related to the size of the eye, hence the optimum length for the human adult is 25 mm, for children is about 15 to 18 mm and for newborn babies is 10 mm in length.

In general, for adults, the lengths of the upper fornix and lower fornix are about 45 to 50 mm and 35 to 40 mm respectively. Thus an insert device of the present invention with a length of up to 35 mm may remain in the upper fornix and one with a length of up to 25 mm may remain in the lower fornix without causing discomfort.

Examples of ophthalmic drugs include antibiotics such as tetracycline, chlortetracycline, bacitracin, neomycin, polymyxin, gramicidin, cephalexin, oxytetracycline, chloramphenicol, kanamycin, rifampicin, tobramycin, gentamicin, erythromycin and penicillin; antibacterials such as sulfonomides, sulfadiazine, sulfacetamide, sulfamethizole and sulfisoxazole, nitrofurazone and sodium propionate; antivirals including idoxuridine, trifluorothymidine, acyclovir, gancyclovir and interferon; non-antibiotic, anti-infection, anti-bacterial or anti-microbial drugs such as iodine based preparation triclosan, chlorhexidine,et al; anti-allergenics such as sodium cromoglycate, antazoline, methapyriline, chlorpheniramine, cetirizine and prophenpyridadine; anti-inflammatories such as hydrocortisone, hydrocortisone acetate, dexamethasone, dexamethasone 21-phosphate, fluorocinolone, medrysone, prednisolone acetate, fluoromethalone, betamethasone, and triamcinolone and non-steroidal agents such as indomethacin, diclofenac, flurbiprofen, piroxicam, ibuprofen and acetylsalicylic acid; decongestants such as phenylephrine, naphazoline and tetrahydrozoline: miotics and anticholinesterase such as pilocarpine, acetylcholine chloride, physostigmine, eserine, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; immunological drugs such as vaccines and immune stimulants; hormonal agents such as estrogens, estradiol, progestational, progesterone, insulin, calcitonin, parathyroid hormone and peptide, vasopressin, hypothalamus releasing factor; beta adrenergic blockers such as timolol maleate, levobunclol HCl and betaxolol Hcl; growth factors such as epidermal growth factor and fibronectin; carbonic anhydrase inhibitors such as dichlorphenamide, acetazolamide and methazolamide and other drugs such as prostaglandins, antiprostaglandins, and prostaglandin precursors; angiogenesis inhibitors such as steroids, angiostatin, antiproliferative agents such as flurouracil and mitomycin.

The drugs may be used in conjunction with a pharmaceutically acceptable carrier. Examples of pharmaceutically acceptable carriers include solids such as starch, gelatin, sugars, e.g., glucose, natural gums, e.g., acacia, sodium alginate, carboxy-methyl cellulose, polymers, e.g., silicone rubber; liquids such as sterile water, saline, dextrose, dextrose in water or saline; condensation products of castor oil and ethylene oxide liquid glyceryl triester of a lower molecular weight fatty acid; lower alkanols; oils such as corn oil, peanut oil, sesame oil, and the like, with emulsifiers such as mono- or di-glyceride of a fatty acid, or a phosphatide, e.g., lecithin, and the like; glycols; polyalkylene glycols; aqueous media in the presence, of a suspending agent, for example, sodium carboxy-methylcellulose, sodium alginate, poly(vinylpyrrolidone), alone, or with suitable dispensing agents such as lecithin, polyclylic acid derivatives polyoxyethylene stearate. The carrier may also contain adjuvants such as preserving, stabilizing, wetting or emulsifying agents.

The mechanism of controlled sustained drug release into the eye is for example diffusion, osmosis or bio-erosion and these mechanisms are described for example in U.S. Pat. No. 4,186,184 and in "Therapeutic Systems" by Klaus Heilmann published by Georg Thieme, Stuttgart 1978.

The period of controlled sustained release is for example up to 7 to 14 days or longer.

In one exemplary embodiment of the present invention utilizing the diffusion mechanism, the configuration of the body of the insert device defines a reservoir for the drug which is in liquid or gel form. At least the lateral wall is a membrane permeable by diffusion so that the drug is released continuously at a controlled rate through the membrane into the tear fluid.

In one exemplary embodiment of the invention utilizing the osmosis mechanism, the device comprises a transverse impermeable elastic membrane dividing the interior of the device into a first compartment and a second compartment; the first compartment is bounded by a semi-permeable membrane and the impermeable elastic membrane, and the second compartment is bounded by an impermeable material and the elastic membrane. There is a drug release aperture in the impermeable and wall of the device.

The first compartment contains a solute which cannot pass through the semi-permeable membrane and the second compartment provides a reservoir for the drug which again is in liquid or gel form.

When the device is placed in the aqueous environment of the eye, water diffuses into the first compartment and stretches the elastic membrane to expand the first compartment and contract the second compartment so that the drug is forced through the drug release aperture.

In one exemplary embodiment of the invention utilizing the bierosion mechanism, the configuration of the body of the insert device is constituted from a matrix of bioerodible material in which the drug is dispersed. Contact of the device with tear fluid results in controlled sustained release of the drug by bioerosion of the matrix. The drug may be dispersed uniformly throughout the matrix but it is believed a more controlled release is obtained if the drug is superficially concentrated in the matrix.

In another embodiment of the invention, there is employed a solid non-erodible body with pores and dispersed drug. The release of drug can take place via diffusion through the pores. Controlled release can be further regulated by gradual dissolution of solid dispersed drug within this matrix as a result of inward diffusion of aqueous solutions.

Examples of the materials for a permeable membrane for the diffusion mechanism include but are not limited to insoluble microporous materials of polycarbonates, polyvinyl chlorides, polyamides, copolymers of polyvinyl chloride and acrylonitrile, polyethylene, polypropylene, polysulphones, polyvinylidene fluorides, polyvinyl fluorides, polychloroethers, polyformaldehydes, acrylic resins, polyurethanes, polyimides, polybenzimadozoles, polyvinyl acetates, polyethers, cellulose esters, porous rubbers, cross-linked poly (ethylene oxide), cross-linked polyvinyl pyrrolidone, cross-linked poly (vinyl alcohol) and polystyrenes.

The drug in liquid or gel form for the diffusion mechanism comprises a diffusion medium which also serves as a pharmaceutical carrier and in which the active ingredient of the drug is dissolved or suspended; the active ingredient is preferably of no more than limited solubility in the medium. Examples of diffusion media include saline, glycerin, ethylene glycol, propylene glycol, water (which may also contain emulsifying and suspending agents), mixtures of propylene glycol monastearate and oils, gum tragacanth, sodium alginate, polylvinyl pyrrolidone), polyoxyethylene stearate, fatty acids and silicone oil.

Examples of materials for an osmotic semi-permeable membrane include but are not limited to cellulose acetate and its derivatives, partial and completely hydrolysed ethylene-vinyl acetate copolymers, highly plasticized polyvinyl chloride, homo- and copolymers of polyvinyl acetate, polyesters of acrylic acid and methacrylic acid, polyvinyl alkyl ethers, polyvinyl fluoride; silicone polycarbonates, aromatic nitrogen-containing polymeric membranes, polymeric epoxides, copolymers of an alkylene oxide and alkyl glycidyl ether, polyurethanes, polyglycolic or polyacetic acid and derivatives thereof, derivatives of polystyrene such as poly(sodium styrenesulfonate) and poly (vinyl benzyltrimethyl-ammonium chloride), ethylene-vinyl acetate copolymers.

Examples of solutes which cannot pass through the semipermeable membrane in an osmotic mechanism include but are not limited to water-soluble inorganic and organic salts and compounds such as magnesium sulfate, magnesium chloride, sodium chloride, lithium chloride, potassium sulfate, sodium carbonate, sodium sulfate, lithium sulfate, calcium bicarbonate, sodium sulfate, calcium sulfate, potassium acid phosphate, calcium lactate, magnesium succinate, tartaric acid, acetamide, choline chloride, soluble carbohydrates such as sorbitol, mannitol, raffinose, glucose, sucrose and lactose.

Examples of bioerodible matrix materials include but are not limited to polyesters of the general formula —O—(W)—CO— and mixtures thereof, wherein W is a lower alkylene of 1 to 7 carbons and may include a member selected from the group of alkylenes of the formula —CH$_2$—, or —CH—CH$_2$—, and Y has a value such that the molecular weight of the polymer is from about 4,000 to 100,000. The polymers are polymerization-condensation products of monobasic hydroxy acid of the formula $C_nH_{2n}$(OH) COOH wherein n has a value of 1 to 7, preferably 1 or 2 and the acid is especially lactic acid or glycolic acid. Also included are copolymers derived from mixtures of these acids. Bioerodible materials also include poly(orthoesters). These materials have the following general formula:

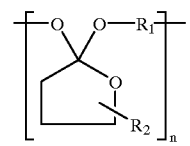

wherein $R_1$ is an alkylene of 4 to 12 carbons, a cycloalkylene of 5 to 6 carbons substituted with an alkylene of 1 to 7 carbons and an alkyleneoxy of 1 to 7 carbons, and $R_2$, is a lower alkyl of 1 to 7 carbons.

Other bioerodible matrix materials which may be employed include but are not limited to the following:

(1) Polyanhydrides such as poly(p-carboxyphenoxy) alkyl (e.g. p-carboxyphenoxypropane) or polymeric fatty acid dimer (e.g. poly-dodecanedioic acid) compounds and further copolymers with sebacic acid, or phthalic acid such as disclosed in Chasin et al., Polyanhdrides for Controlled Drug Delivery, *Biopharm.*, February 1988, 33–46; and Lee et al. (1988), The Use of Bioerodible Polymers and 5 fluorouracil in Glaucoma Filtration Surgery, *Invest. Ophthalmol. Vis. Sci.*, 29, 1692–1697;

(2) Poly (alkyl-2-cyanoacrylates) such as poly (hexyl-2-cyancacrylate) as described by Douglas et al. (1987), Nanoparticles in Drug Delivery, *CRC Crit. Rev. Therap. Drug Carr. Syst.*, 3, 233–261; and (3) Polyamino acids such as copolymers of leucine and methyl glutamate.

Further information on membrane and bioerodible materials is contained in U.S. Pat. Nos. 3,828,777 and 4,186,184 and also the following references: Leong and Langer (1987), Polymeric Controlled Drug Delivery, *Adv. Drug Del. Rev.*, 1, 199–233; and Smith et al. (1990), Bioerodible Polymers for Delivery of Macromolecules, *Adv. Drug Del. Rev.*, 4, 343–357.

Examples of materials for use as non-erodible rods include but are not limited to polymers such as hydroxyethylmethacrylate and further co-polymers with methacrylic acid, methylmethacrylate, N-vinyl 2-pyrrolidone, allyl methacrylate, ethylene glycol dimethacrylate, ethylene dimethacrylate, or 1,1,1 trimethylopropane trimethacrylate, and dimethyl diphenyl methylvinyl polysiloxane.

Accordingly to a second, independent, aspect of the present invention a flexible ocular insert device adapted for the controlled sustained release of two or more drugs upon insertion into the upper or lower fornix of the eye, said device comprising an elongate body of a polymeric material including two end portions said body containing a pharmaceutically active ingredient, said device having a length of at least 8 mm and a maximum diameter not exceeding 1.9 mm, wherein said device is sufficiently flexible to allow it to bend along the curvature of the eye within the upper or lower fornix upon being positioned so that the longitudinal axis of said device is generally parallel to the transverse diameter of the eyeball, said device being of a size and configuration such that, upon insertion into the upper or lower fornix, the device does not extend onto any visible portion of the eyeball, and in which at least two distinct portions of the device include respective distinct ones of said drugs.

This permits the use of synergistic, additive, supportive or complementary drugs for improved patient treatment in which the drugs are not mixed before release but which mix in the eye after independent release from the device. This avoids the need for regulatory studies on the mixture for antagonism and so on.

The different drug's release rates can be adjusted to be optimal for each drug by independently tailoring the characteristics of the different drug bearing elements of the device.

It should be noted that this aspect of the invention does not require the device to have tapered end portions or anchoring protrusions, these being entirely optional features as regards the invention is its second aspect.

On the other hand, all the embodiments of tapered end portion devices described in relation to the tapered end portion devices according to the first aspect of the present invention may also incorporate the invention in this second aspect by forming distinct portions of each of these embodiments with distinct respective drugs for controlled release of those distinct drugs.

Such multiple drug devices can be made by the same methods described in relation to the single drug release embodiments with suitable modifications. For example, they may be formed by injection molding in which each distinct material is forced into the device mold via distinct passageways so the distinct drug containing portions of the device are formed simultaneously as portions of a unitary device.

Alternatively, the distinct drug portions may be formed by separate molding processes as employed in a single drug delivery system and the portions joined together to form the final device, eg by use of a suitable adhesive.

BRIEF DESCRIPTION OF THE DRAWINGS

Exemplary embodiments of the present invention according to both aspects will now be described with reference to the accompanying drawings of which:

FIGS. 4a, 5a and 6a are diagrammatic views of a different flexible ocular insert devices according to first aspect of the present invention for insertion in the adult upper fornix;

FIGS. 4b, 5b and 6b are diagrammatic views of a different flexible ocular insert devices according to a first aspect of the present invention for insertion in the adult lower fornix;

FIGS. 18–21 depict graphs of the present invention.

Figure 1:
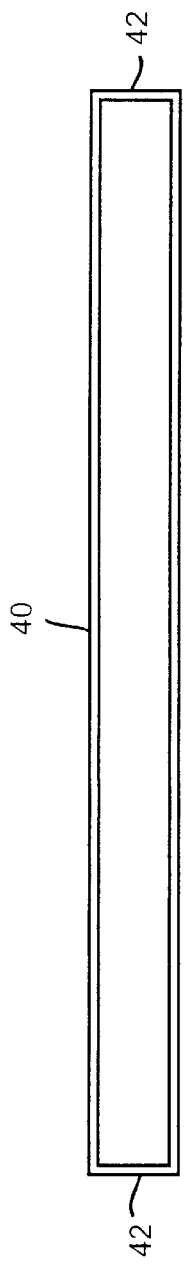
FIG. 1 is a diagrammatic sectional view of a prior art diffusional ocular insert device.

The ocular inserts of FIGS. 4 to 9 will first be described in terms of their overall external configuration.

DETAILED DESCRIPTION OF PREFERRED EMBODIMENTS

In the embodiment of FIGS. 4a, the device has two substantially right circular cone end-portions 2 which have a common base of diameter 1.4 mm at the centre of the device and rounded apexes 3. Purely optional projections 4 are about 1 mm wide and are formed about 0.2 mm proud of the body of the device and spaced about 10 mm apart.

The embodiment of FIG. 5a, like that of FIG. 4a, is in the shape of a joined pair of cones with base diameters of 1.4 mm but in this case the cones are oblique circular cones 5 with the apexes 6 such as to provide the device with one straight, longitudinal edge 8. Optional projections 9, where present, may be positioned and dimensioned as shown by the dotted lines.

Figure 6A:
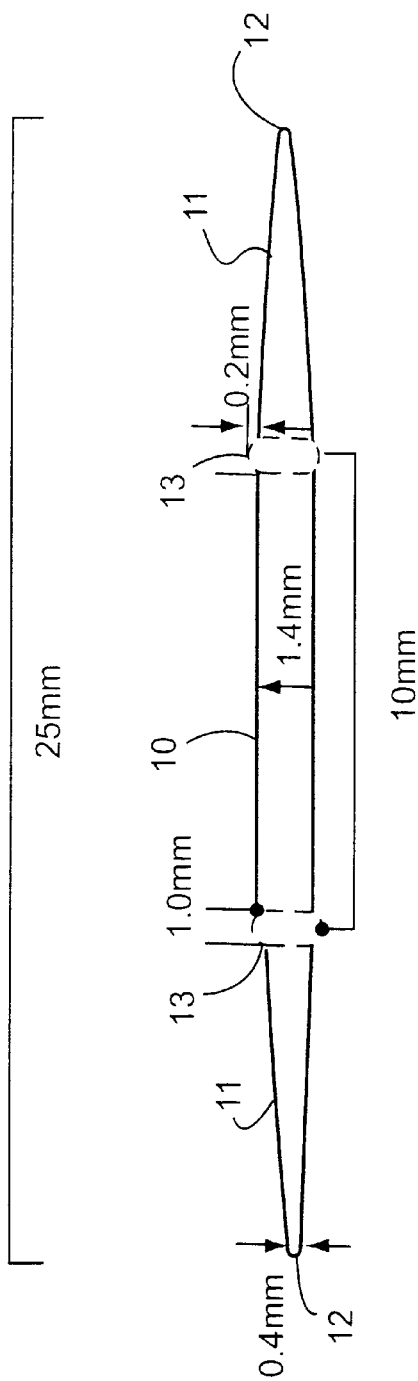

The insert may, alternatively, as shown in FIG. 6a have a body comprising a central cylindrical portion 10, for example, approximately 10 mm long and 1.4 mm in diameter and at each end an end portion 11, each in the form of a substantially right circular cone, 7.5 mm in length with circular cross-sections reducing from 1.4 mm diameter at the end adjacent the cylindrical portion to about 0.4 mm at the outer extremity adjacent a rounder apex 12. It again may also include optional projections 13 as described in relation to the FIG. 4a and 5a embodiments.

Figure 6B:
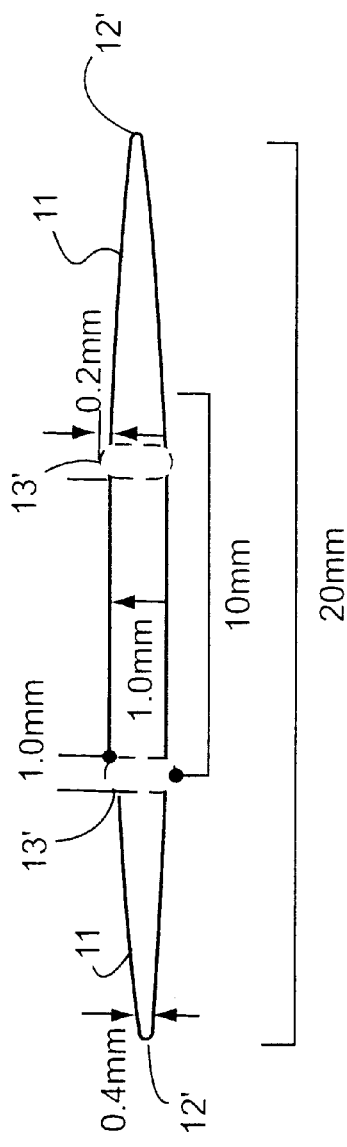

The devices of FIGS. 4b, 5b and 6b are configured as the devices shown in FIGS. 4a, 5a and 6a (with common features being the same reference numerals primed) but with the dimensions of the body reduced so as to be suitable for insertion in the lower fornix of an adult, the overall lengths of each device being 20 mm and maximum diameter being 1.0 mm. The optional toroidal projections 4, 9 or 13, when present, are as in the embodiments of FIGS. 4a, 5a and 6a, symmetrically located on the body of the device 10 mm apart and 0.2 mm proud of the body surface.

Figure 7:
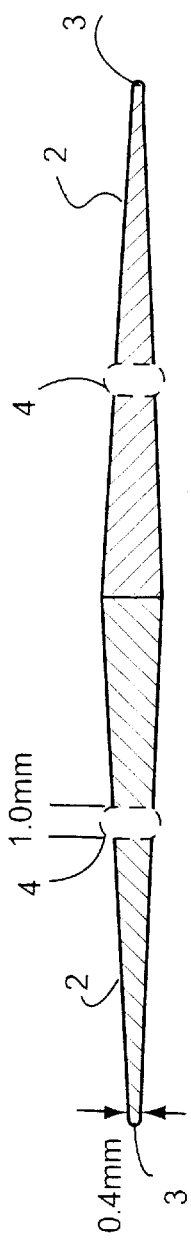
FIGS. 7 and 8 are diagrammatic views of a different flexible ocular insert devices according to second, independent, aspect of the present invention.
Figure 8:
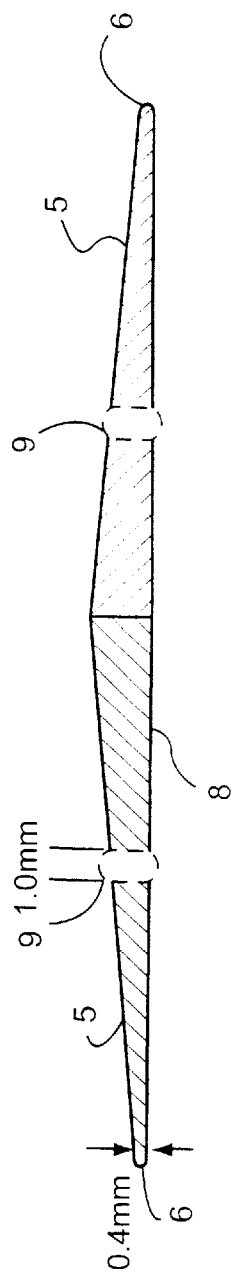

The embodiment of FIG. 7 and 8 are configured as those of FIGS. 4a and 5a but differ in that the two halves release distinct drugs in use, whereas the former devices release only one drug. The different drug release portions of FIGS. 7 and 8 are indicated by the different shading. The device of FIG. 6a as well as the lower fornix devices 5a, 5b and 6b can also be formed as a dual drug release device.

Figure 9:
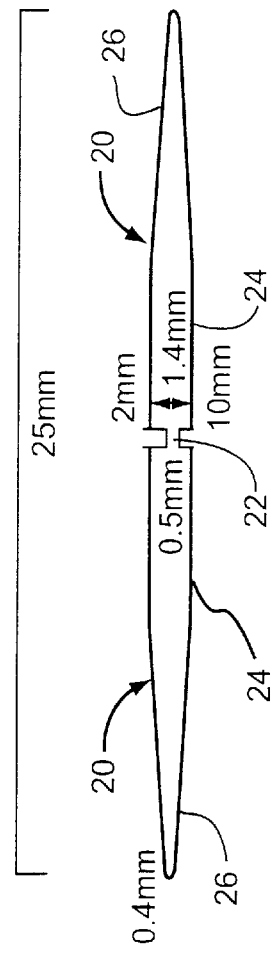
FIG. 9 is a diagrammatic view of a different flexible ocular insert device according to the second aspect of the present invention.
Figure 10:
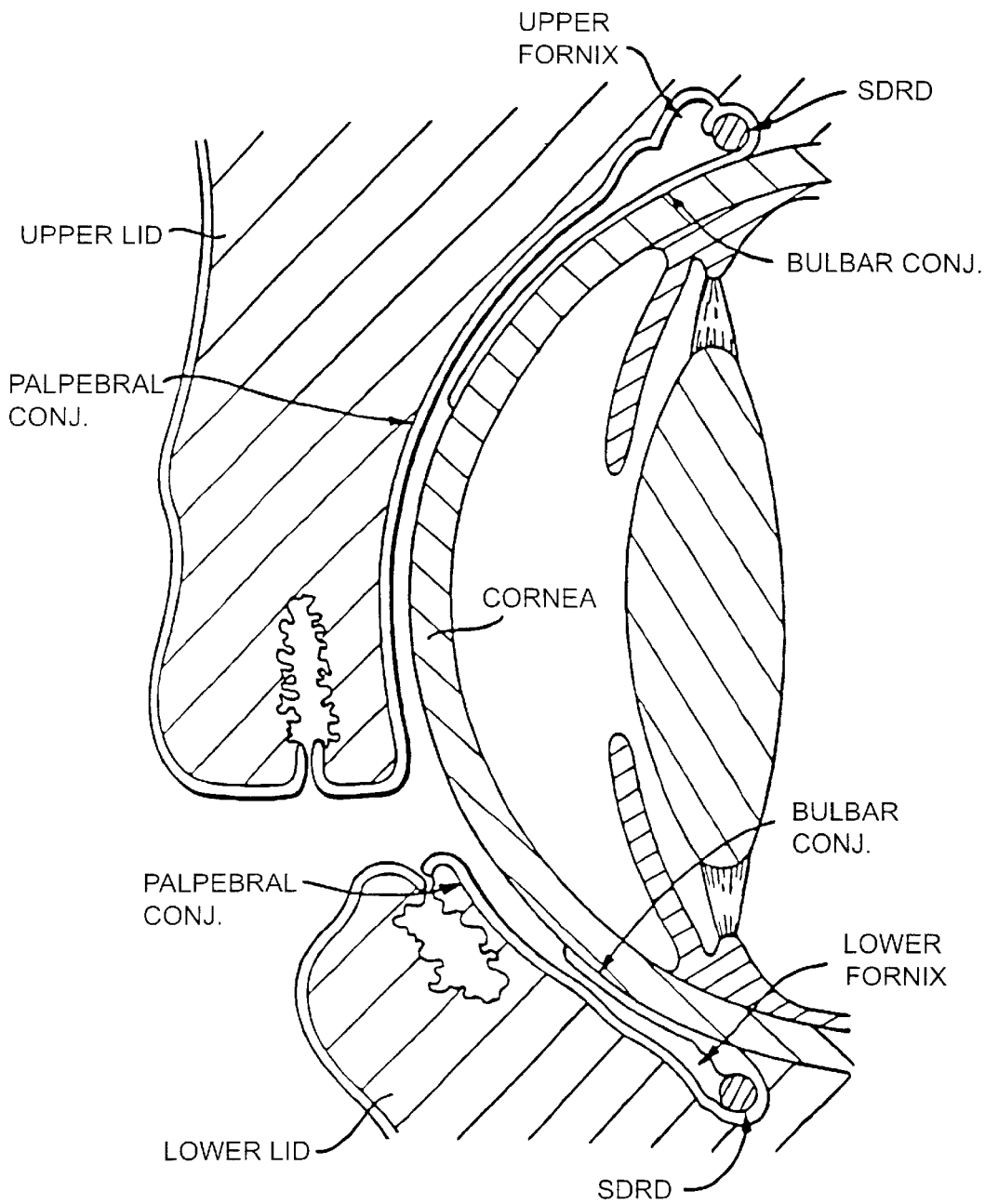
FIG. 10 is a diagrammatic sectional view of the eye with an ocular insert device of the present invention installed in the upper and lower fornix.
Figure 11:
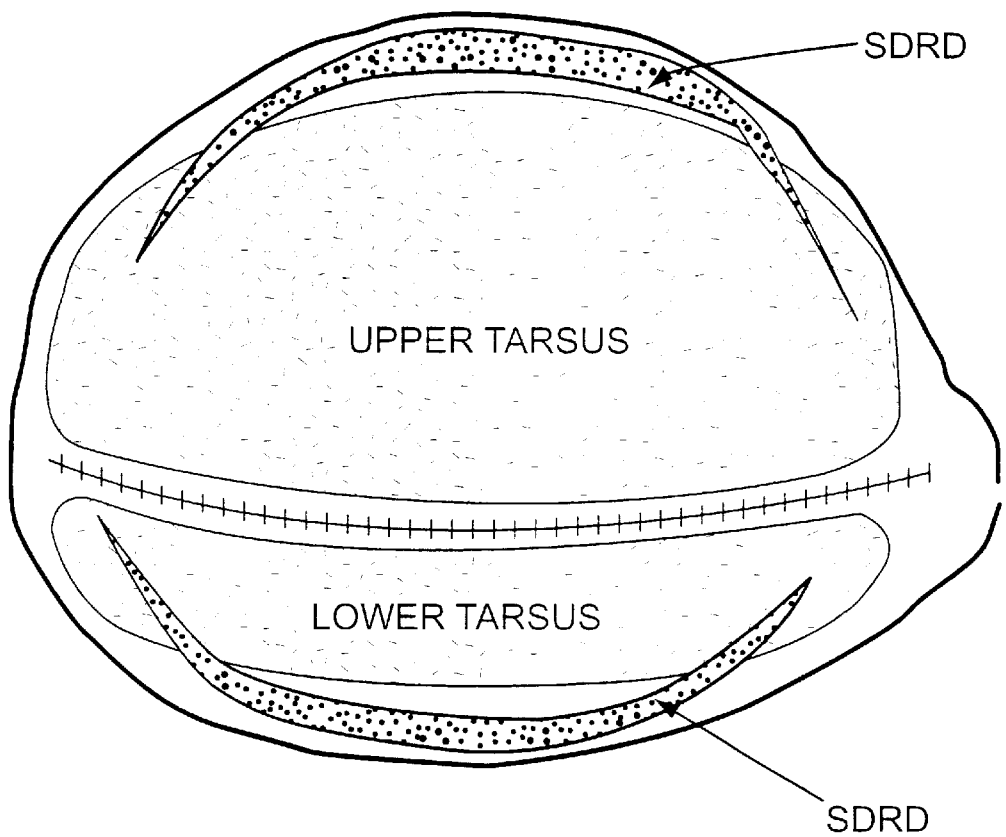
FIG. 11 is a diagrammatical front view of an eye with an ocular insert device of the present invention installed in the upper and lower fornix.
Figure 12:
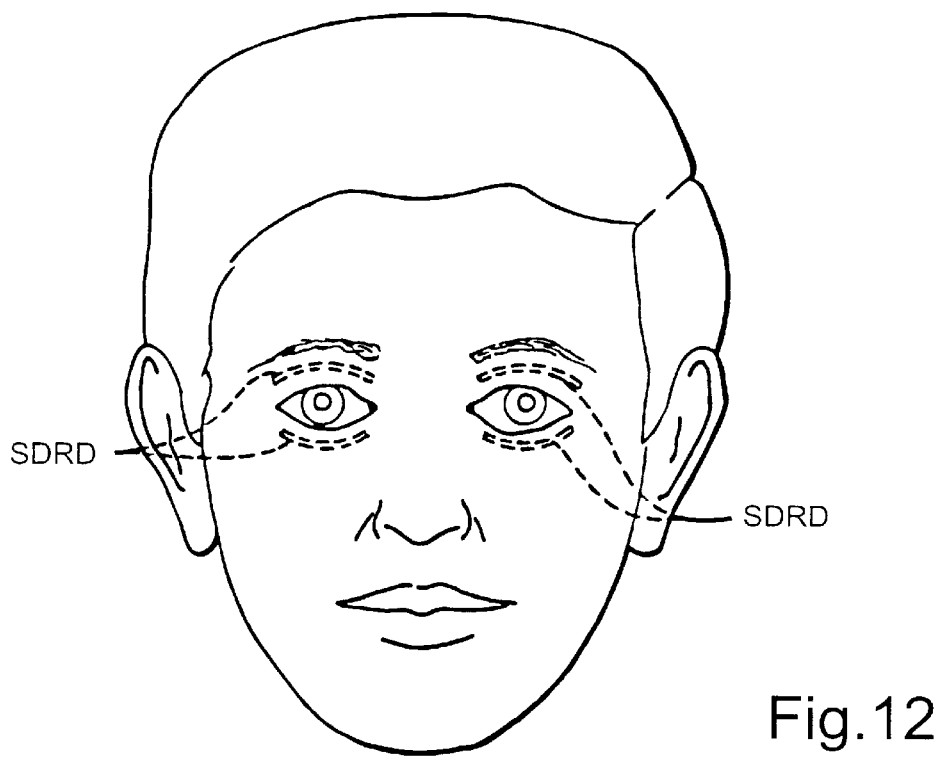
FIG. 12 is a representation of the head of a patient with the location of the installed ocular insert device shown in dashed lines.
Figure 13:
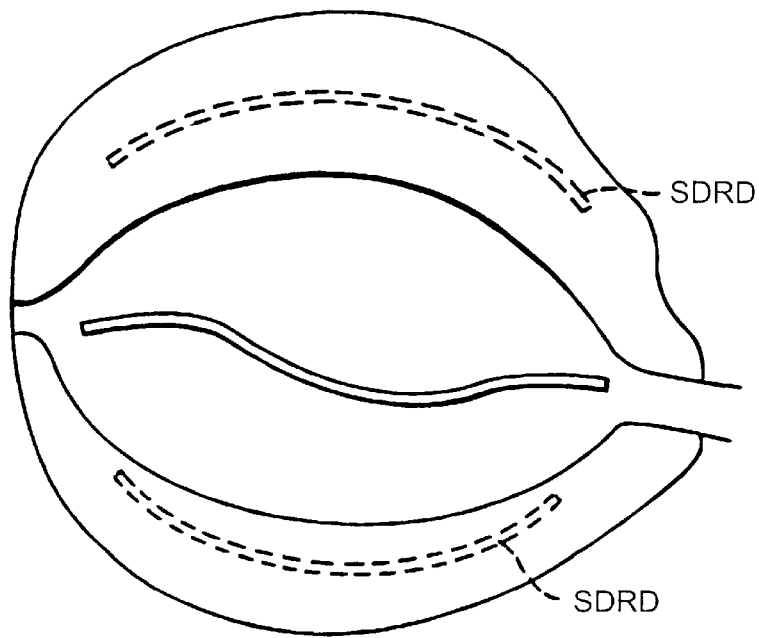
FIG. 13 is a diagrammatic view of the position of the installed ocular insert device in a closed eye.
Figure 14:
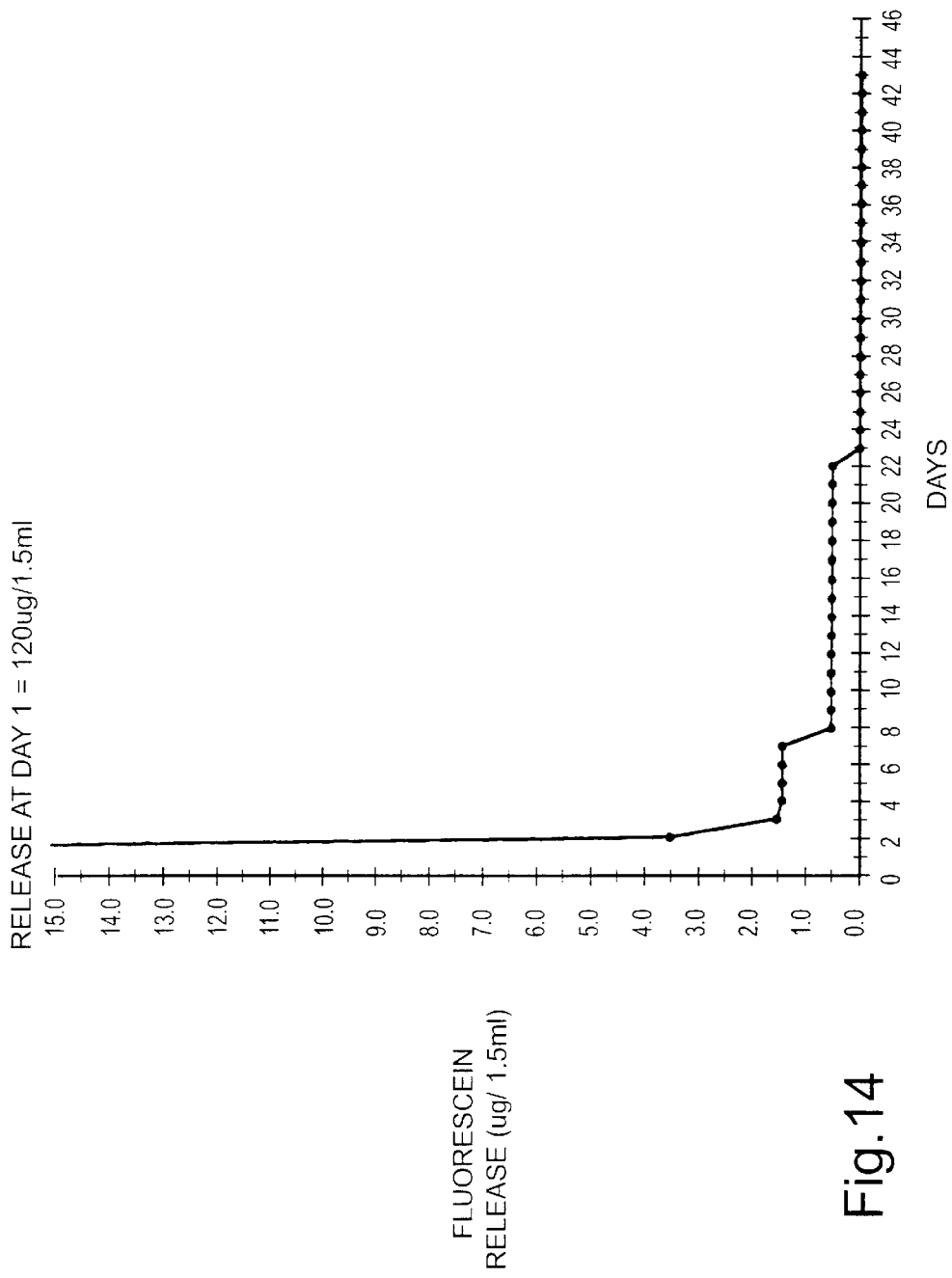
FIGS. 14 to 17 are graphs showing data on drug release rates of devices according to the present invention.
Figure 15:
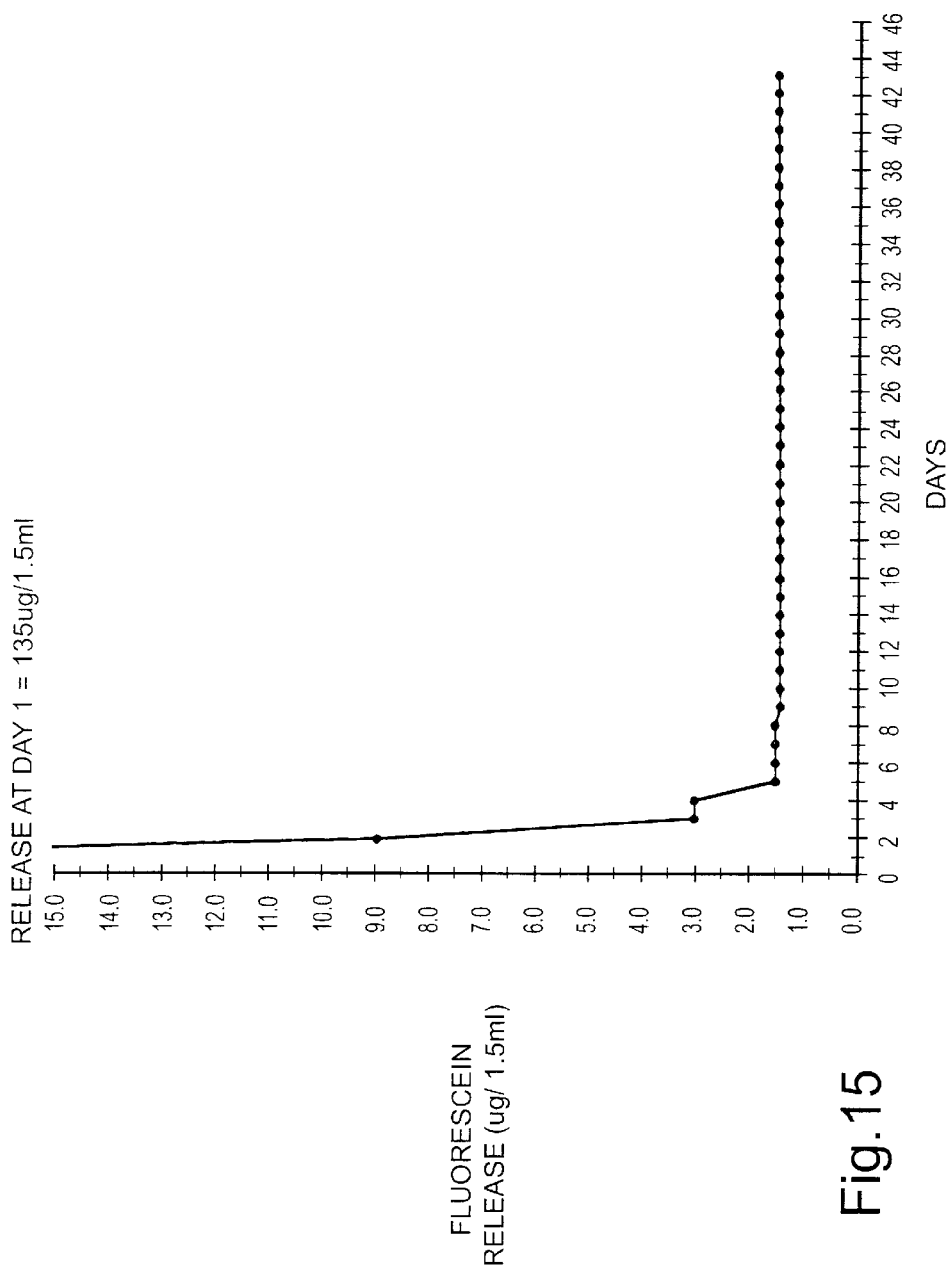
Figure 16:
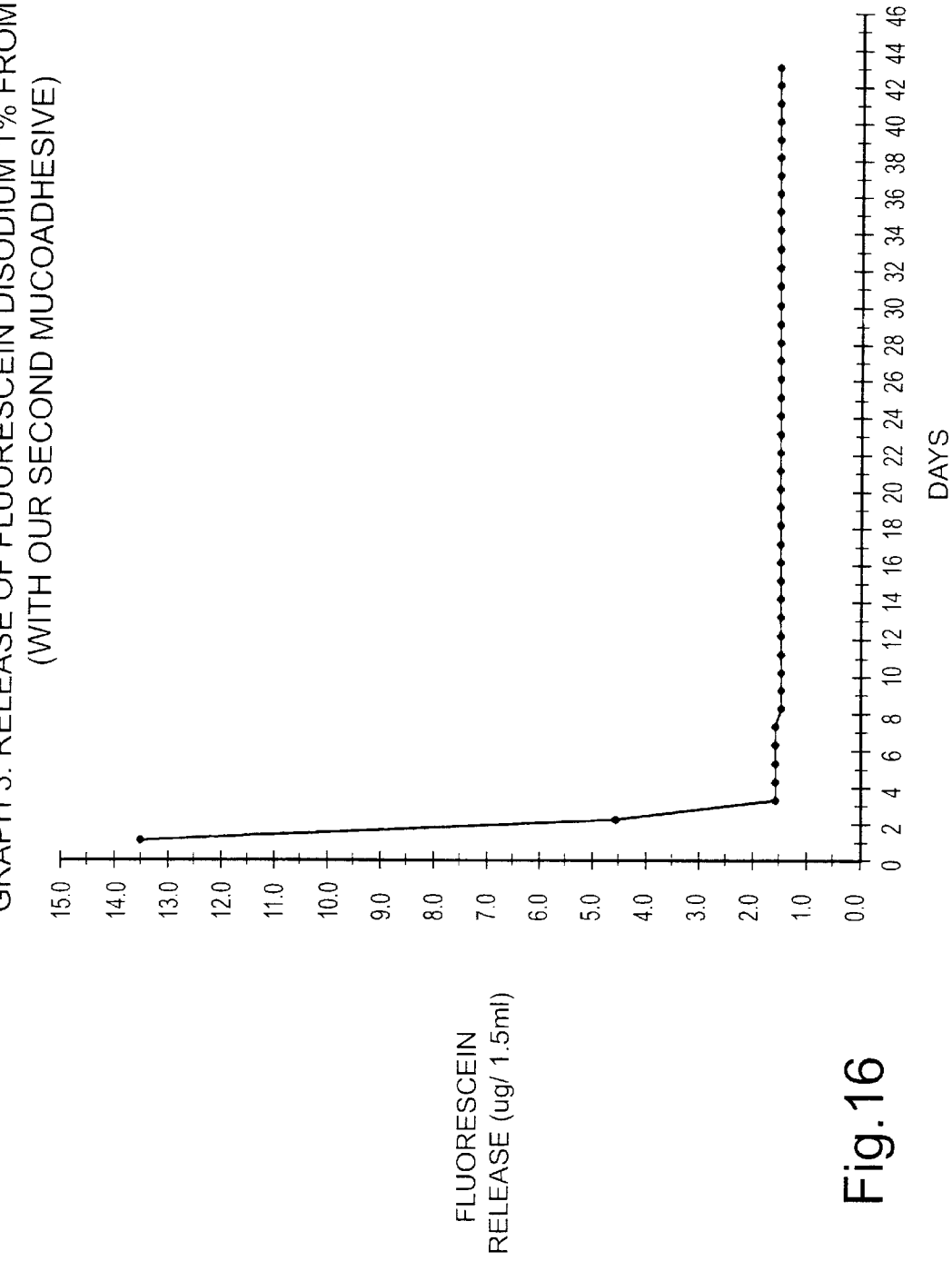

FIG. 9 shows a further embodiment of the present invention in which the device has two similar body portions which are joined by a narrow cylindrical portion 22 of length 2 mm and diameter 0.5 mm. Each body portion is formed as a cylindrical portion 24 with a conical end portion 26 tapering to a 0.4 mm radius apex at the extremity of the device. Each body portion 20 releases a different drug in use.

Figure 2:
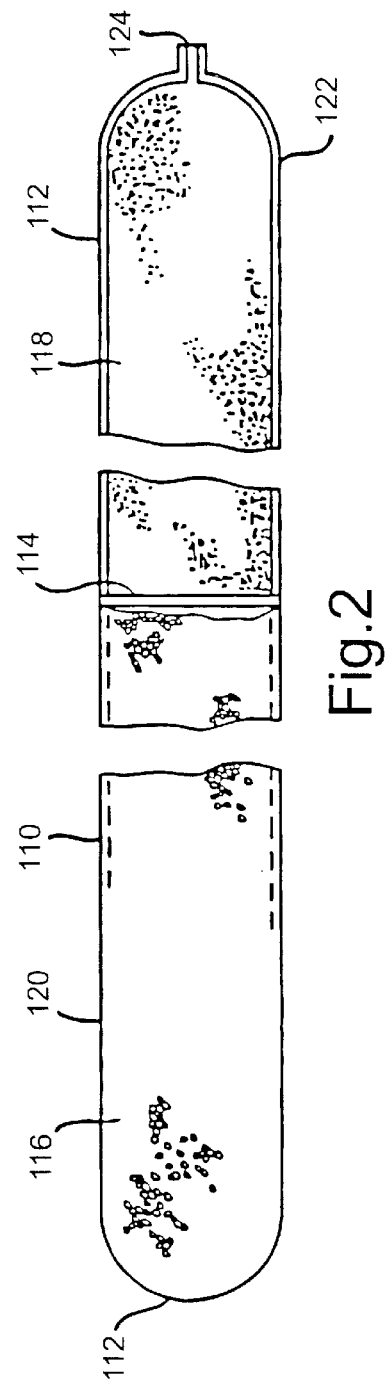
FIG. 2 is a diagrammatic sectional view of a prior art osmotic ocular insert device.
Figure 3:
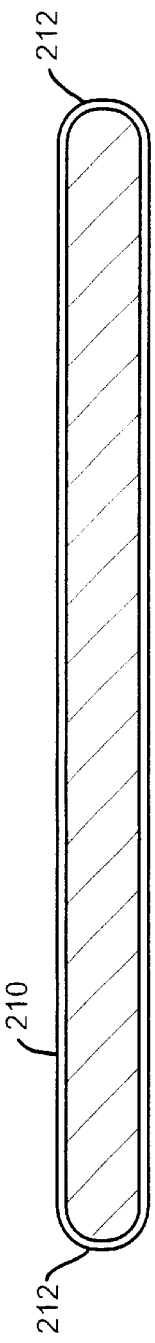
FIG. 3 is an enlarged diagrammatic sectional view of a prior art bioerodible insert device.

FIGS. 1 to 3 will now be described which illustrate various drug release arrangements employable with the present invention in all its aspects.

The prior art ocular insert device shown in FIG. 1 comprises a circular cylindrical wall 40 of a microporous synthetic polymer membrane which is insoluble in tear fluid but is permeable by diffusion. The cylindrical wall 40 is closed by transverse planar end walls 42 which may be of the same microporous synthetic polymer membrane as the cylindrical wall 40 or alternatively may be impermeable. The overall length of the device is 8 to 25 mm or up to 35 mm for the upper fornix and its external diameter 0.5–1.9 mm.

The cylindrical wall 40 and the end walls 42 define a reservoir for a drug which diffuses through the membrane as described hereinbefore.

The prior art ocular insert device shown in FIG. 2 comprises a circular cylindrical wall 110 closed by hemispherical domed end portions 112. The device also comprises, perpendicular to the axis of the cylindrical wall, an impermeable elastic membrane 114 dividing the interior of the device into a first compartment 116 and a second compartment 118. The cylindrical wall 110 comprises different materials as respectively do the end walls 112 so that the first compartment is bounded by a semi-permeable synthetic polymer membrane 120 and the elastic membrane 114 and the second compartment is bounded by an impermeable synthetic polymeric membrane 122 and the elastic membrane 114. There is an axial drug release aperture 124 in the membrane 122 at the domed end portion 112 thereof.

The first compartment 116 contains a solute and the second compartment provides a reservoir for a drug which is forced through the aperture 124 by the stretching of the elastic membrane 114 under osmosis as described hereinbefore.

The prior art ocular insert device shown in FIG. 3 comprises a circular cylindrical body 210 with domed end portions 212. The device is constituted from a matrix of synthetic polymeric bioerodible material in which a drug is dispersed, being concentrated superficially of the matrix for controlled release therefrom as the matrix bioerodes.

The device having the configuration as shown in FIG. 3 may also be constituted of a solid non-erodible material having pores and dispersed drug as previously discussed.

The overall length and diameter of each of the devices of FIG. 2 and FIG. 3 is the same as for the device of FIG. 1.

The drug release techniques adopted by these prior art devices may all be used in relation to the devices of the present application.

The ocular insert device of the present invention may be installed in the fornix by the method as follows.

METHOD OF INSERTING DEVICE IN THE UPPER AND LOWER FORNIX OF THE EYE

1 Method of Inserting the Device in the Upper Fornix
1.1 Anaesthetise the eye with a drop of a chosen anaesthetic.
1.2 Ask patient:
  to sit on a chair.
  move the head slightly backward (30° approximately).
  look down continuously.
1.3 Hold the device with suitable forceps in a slightly off centre position, leaving about 6–7 mm of the device free beyond the lips of the forceps.
1.4 Lift the upper lid upward and backward to produce a gap of 3 mm approximately between the lid and the eye.
1.5 Insertion into the fornix:
  Insert first the one-half of the device with the free part into the gap between the lid and the eye.
  Align the middle of the device with the middle of the upper fornix by moving the forceps to the left or right.
  Push the forceps whilst still holding the device gently into the deep fornix until reaching the bottom of the fornix.
  Drop the device in the deep fornix and remove the forceps, while holding the upper lid with a finger to the side of the forceps in order to prevent rejection of the device.
1.6 Ask the patient to close his/her eyes, then with the help of the head of the forceps and over the lid manoeuvre the device into the deep fornix. This is to ensure that the device is in the deep fornix.
1.7 Ask the patient to move his/her eye up, down and laterally 2 to 3 times. This is to ensure that the device is in the deep fornix and not moving with the eye movement.
2 Method of Inserting the Device in the Lower Fornix
2.1 Anaesthetise the eye with a drop of a chosen anaesthetic.
2.2 Ask patient:
  to sit on a chair.
  move the head slightly backward (30° approximately).
  look up continuously.
2.3 Hold the device with suitable forceps in a slightly off centre position, leaving about 5–6 mm of the device free beyond the lips of the forceps.
2.4 Pull the lower lid down and forward to produce a gap of 3 mm approximately between the lid and the eye. 2.5 Insertion into the fornix.
  Insert first the one-half of the device with the free part into the gap between the lid and the eye.
  Align the middle of the device with the middle of the lower fornix by moving the forceps to the left or right.
  Push the forceps whilst still holding the device gently into the deep fornix until reaching the bottom of the fornix.
  Drop the device into the deep fornix and remove the forceps whilst lifting the lower lid upward and inward against the forceps in order to prevent rejection of the device.
2.6 Ask the patient to close his/her eyes, then with the help of the forceps and over the lid manoeuvre the device into the deep fornix. This is to ensure that the device is in the deep fornix.
2.7 Ask the patient to move his/her eye up, down and laterally 2 to 3 times. This is to ensure that the device is in the deep fornix and not moving with the eye movement.

Upon installation, the ocular insert device will be positioned in the upper or lower fornix in one of the positions identified as "SDRD" as shown in FIGS. 10 to 13 of the drawings.

At least two protrusions should be present (where employed) with a view toward providing an overall symmetrical shape for the device. In the case where only two protrusions are employed, such protrusions should be evenly spaced relative to the length of the device so that the protrusions will be equidistant from their respective ends of the device. Where more than two protrusions are employed, it is important to provide a symmetrical arrangement with even spacing so as to achieve a uniform anchoring function along the length of the device.

The ocular insert device of the present invention may be formed with a polygonal or circular cross section, for example.

The drug loaded device can be formed by any of various known processes such as extrusion molding, injection molding, transfer molding or compression molding.

In carrying out the extrusion molding process, polymer material is, typically, blended with drug at ratios of drug up to 40% by weight on a cooled two roll mill and then fed into a screw drive extruder. By the action of the single flight screw with diminishing pitch and a length to diameter ratio of about 12:1 to 10:1, material is continuously forced out through a coin or plate die (port) with openings conforming to the shape and dimensions of the subject device (i.e. circular). For designs involving tube configurations, a mandrel held in place by a spider flange is positioned prior to the die. The continuous noodle is pulled via conveyer belt through a heated horizontal or vertical chamber (315 to 425 degrees C.) to achieve vulcanization of the material. The final device is made by a cutting apparatus where the rods are cut to size. Additional modifications such as polishing the ends of the device can be accomplished.

In carrying out the transfer molding process, the blend of polymer material and drug is placed into a heated transfer press with an aluminum or stainless steel mold containing impressions of the proper shape and size. The material is forced into the mold at between 200 and 4000 psi. The mold itself is kept under 10 tons of clamp pressure. The mold is kept heated and under pressure at any of the following conditions:

| | |
|---|---|
| 4–10 minutes | 135 degrees C |
| 15 minutes | 100 degrees C |
| 30 minutes | 75 degrees C |
| 2 hours | 55 degrees C |
| 5 hours | 40 degrees C |
| 24 hours | Ambient temperature (25 degrees C) |

The mold is cooled, separated and the formed devices are then removed.

Multiple drug delivery devices according to the second aspect of the present invention are conveniently formed by injection molding with the distinct drug loaded materials being injected separately, but simultaneously, into the mold via respective passageways.

Silicone rubbers/elastomers may be employed as the material from which the devices are formed. The silicone rubbers/elastomers may be prepared as follows:

Silicone rubber prepared using dimethylsiloxane polymer or dimethyl and methylvinyl siloxane copolymers, reinforcing silica, platinum catalyst, inhibitor and siloxane crosslinker and other vulcanizing agents such as organic peroxides is either hand mixed, mixed on a two roll mill, or injection molded together with micronized drug (predominantly 10 micron particles or less). Drug is loaded into the polymer mixture at levels up to 40 weight percent of the total weight together with any other necessary excipients or release modifiers such as glycerin or sorbitol. Entrapped air within the mixture is removed by exposure to a vacuum of about 28 inches of mercury (94.8 kPa) for approximately 30 minutes. Drug is solidified within the polymer matrix by curing (vulcanizing) the mixture while being molded into the desired shape.

The devices may also be formed of bioerodible polymers prepared as follows:

Solid mixtures of bioerodible polymers (Polyhydroxyacids such as polylactic acid and polyglycolic acid, and polyhydroxybutyrate; Polyesters and polyorthoesters including cyclic ortho-esters with dials or diketeneacetals or diacids with dials or polyols; Polyanhydrides made from one or more of the following: p-carboxyphenoxy propane, p-carboxyphenoxy hexane, sebacic acid, dodecanedioic acid, 1,4- phenylenedipropionic acid, isophthalic acid, polypropylene fumarate and polypropylene maleate; Polypeptides; and Polycyanoacrylates) can be admixed with up to about 60% by weight of drug. The material can be compressed in aluminum or stainless steel molds situated in a Carver hydraulic press at 12 tons of pressure for at least 15 minutes at 100 degrees C.

As a further example, the devices may be formed of methacrylate hydrogels prepared as follows:

Hydrogels loaded with drug can be constructed from crosslinked methacrylate polymers which include compositions containing one or more of the following: 2-hydroxyethyl methacrylate (HEMA), ethylene glycol dimethacrylate, polymethylmethacrylate, methylmethacrylate, glycol monomethacrylate, ethylene monomethacrylates, glycol dimethacrylates, vinylpyrrolidone, methacrylic acid, divinylbenzene, and alkyldiol methacrylates, acrylamide, methylene bis acrylamide.

Various crosslinking percentages can be achieved by altering the ratios of the copolymers. For example a 40:1 weight ratio of acrylamide to methylene bis acrylamide produces a 2.5%. crosslinking. A buffered solution (pH 7–9) of the copolymers is made containing the desired crosslinking ratio. The final total polymer percentage can be varied from 1 to 25%. Drug is admixed into this solution. Suitable crosslinking free radical generator and catalyst (such as ammonium persulfate and tetra methyl ethylene diamine) is added. The mixture is poured into an appropriate mold with the desired shape. Polymerization occurs within 30 minutes.

These embodiments of the invention may employ the drugs and pharmaceutically acceptable carriers as previously described.

The following are specific examples which may be carried out in accordance with the present invention.

EXAMPLE 1

One part of silastic MDX4-4210 curing agent (Dow Corning Corp, Midland, Mich.) is mixed with 10 parts of MDX4-4210 Silastic base elastomer (Dow Corning Corp, Midland, Mich.). The material is placed under vacuum of about 28 inches of mercury (94.8 kPa) for 30 minutes. Material is then transferred into a cylinder situated in a transfer press. The material is then forced into a 12 cavity aluminum mold heated to 135 degrees C. which contained impressions of the ribbed device design and forced into the mold at a transfer pressure of 400 psi (2757.9 kPa) for 3.5 minutes. The mold itself is kept under 10 tons of clamp pressure. The mold is cooled, separated and the formed devices are removed. The devices are cleaned by soaking in isopropyl alcohol for approximately 5 minutes and allowed to air dry.

EXAMPLE 2

One part of silastic MDX4-4210 curing agent (Dow Corning Corp, Midland, Mich.) is mixed with 10 parts of MDX4-4210 silastic base elastomer (Dow Corning Corp, Midland, Mich.). Oxytetracycline hydrochloride (Sigma Chemical Co., St. Louis) in the amount of 10% by weight of the total mixture is thoroughly blended in with care taken to minimize entrapment of air. The material is placed under vacuum of about 28 inches of mercury (94.8 kPa) for 30 minutes. Material is then transferred into a cylinder situated in a transfer press. The material is then forced into a 12 cavity aluminum mold heated to 135 degrees C. which contained impressions of the device design and forced into the mold at a transfer pressure of 400 psi (2757.9 kPa). The mold itself is kept under 10 tons of clamp pressure for 3.5 minutes. The mold was cooled, separated and the formed devices are removed.

EXAMPLE 3

One part of Silastic MDX4-4210 curing agent (Dow Corning Corp, Midland, Mich.) is, mixed with 10 parts of MDX4-4210 Silastic base elastomer (Dow Corning Corp, Midland, Mich.). Oxytetracycline hydrochloride (Sigma Chemical Co., St. Louis) in the amount of 20% by weight of the total mixture was thoroughly blended in with care taken to minimize entrapment of air. The material is placed under vacuum of about 28 inches of mercury (94.8 kPa) for 30 minutes. Material is then transferred into a cylinder situated in a transfer press. The material is then forced into a 12 cavity aluminium mold heated to 121 degrees C. which contained impressions of the tapered, device design and forced into the mold at a transfer pressure of 800 psi (5515.8 kPa). The mold itself is kept under 10 tons of clamp pressure for 3.25 minutes. The mold was cooled, separated and the formed devices are removed.

EXAMPLE 4

Silastic medical grade ETR elastomer Q7-4720 (Dow Corning Corp, Midland, Mich.) is prepared by first individually softening Part B and Part A of the elastomer on a cooled two-roll mill. The two components are then blended together in a 1:1 ratio on the two-roll mill. Material was then transferred into a cylinder situated in a transfer press. The material is then forced into a 12 cavity aluminum mold heated to 121 degrees C. at a transfer pressure of 800 psi (5515.8 kPa). The mold itself is kept under 10 tons of clamp pressure for 3.25 minutes. The mold is cooled, separated and the formed devices are removed.

EXAMPLE 5

Medical grade liquid silicone rubber Silastic Q7-4840 A/B (Dow Corning Corp, Midland, Mich.) is prepared by mixing equal portions of the A and B components. A vacuum of 29 inches of mercury (98.2 kPa) is applied to the mixture for 30 minutes to deair the material. The material is compression molded in an aluminum mold in a carver press for 15 minutes at 100 degrees C. under 12 tons of pressure. The mold is cooled, separated, and the devices removed. The devices are cleaned by soaking in isopropyl alcohol for approximately 5 minutes and allowed to air dry.

EXAMPLE 6

Silastic medical grade ETR elastomer LSR 76000 (Dow Corning Corp., Midland, Mich.) is prepared by first individually softening Part B and Part A of the elastomer on a cooled two-roll mill. The two components are then blended together in a 1:1 ratio on the two-roll mill. Oxytetracycline hydrochloride with or without USP grade dextrose premixed in various ratios is added incrementally into the blend to assure homogeneous distribution. Material is then transferred into a cylinder situated in a transfer press. The material is then forced into a 12 cavity aluminium mold heated to 121 degrees C. at a transfer pressure of 800 psi (5515. 3 kPa). The mold itself is kept under 10 tons of clamp pressure for 3.25 minutes. The mold is cooled, separated and the formed devices are removed.

EXAMPLE 7

For control devices not containing any protrusion beyond the core, simple rods were prepared as in Example 1 except using a mold with impressions of a the desired device shape.

EXAMPLE 8

A study was carried out in which the device of the present invention was inserted into the upper or lower fornix of the eyes of human patients with no eye disease by the method described earlier in the application. Results are shown in Tables 1 to 5.

The configuration of the cylindrical device was as shown in FIG. 6b and called the SDRD-3 device. The material employed was a solid silastic based material Nusil MED-4830, a medical grade elastomer. No drug was incorporated into the device.

This study was carried out in the eyes of human volunteers, rather than experimental animals since the size and depths of the upper or lower fornix of experimental animals are different from the human eye. In some animals, the presence and movement of nictitating membrane can dislodge the device.

A Retention in the Upper Fornix

The method of insertion into the upper fornix used in this study was as follows.

The volunteer was asked to sit down, hold his/her chin slightly up and to look down continuously throughout the exercise.

The eye was anaesthetized by a drop of Benoxenate (oxybuprocaine) hydrochloride 0.4% W/V (Smith & Nephew).

The upper lid was separated from the globe by about 4 to 5 millimeters by holding the eyelashes and gently pulling the lid backward and upward. The device, held in the forceps, was centrally located at a midpoint between the nasal and temporal canthus and was pushed under the upper lid inward about 6 to 7 mm. The tip of a finger was positioned in the middle of the eyelid just above the end of the forceps before the device was released and forceps removed. With the tip of a finger, or the upper end of the forceps, the device was gently pushed upward and toward the deep fornix. The manoeuvre was repeated twice more in each corner (canthus). The volunteer was asked to move the eye downward and upward three times.

The volunteer was advised.

(a) If he/she feels that the end of the device was near the inner or outer corner (nasal or temporal canthus) of the eye or feels irritation, he/she can push the device back to the middle of the fornix by closing the eye and looking down, then, with the tip of a finger gently press the corner of the eye.

(b) Repeat manoeuvre explained above once in the morning after waking up and once in the evening before sleeping.

(c) Avoid rubbing the eyes.

(d) It is not possible to visualize the device in the deep fornix but he/she may be aware of sensation in a corner of the eye, relieved by prodding the upper part of the lid with a finger tip after closing the eye.

No additional topical or systemic treatment was given to any of the volunteers. The volunteers were asked to report to the investigator if the device was rejected from the eye. The duration of retention planned for four weeks.

In this study, 25 volunteers with normal eyes were included.

The device was randomly inserted in the upper fornix of the left or right eye in the volunteers.

The period of retention in the upper fornix is shown in appended Tables 1 and 2. In 18 volunteers (72%), the device was retained for 1 week or more. All 18 volunteers retained the device for 28 days or longer before it was removed.

The period of retention of the present invention in comparison with the retention of the Ocufit device presented in U.S. Pat. No. 5,395,618 are shown in appended Table 3. The results show that the present device was retained for 28 days or more in the upper fornix of 72% of volunteers while the Ocufit device was retained for 28 days or more in the upper fornix of between 14% and 47% of volunteers.

B Retention in the Lower Fornix

Twenty five volunteers with normal eyes were included. The device was randomly inserted in the lower fornix of the right or left eye in the volunteers.

The results of the study on the retention of the present device in the lower fornix are shown in appended Tables 4 and 5.

In 11 (44%) of volunteers, the device was retained in the lower fornix for 14 days or more. Of these, 9 volunteers (36%) retained the device for 28 days or more. In comparison, the Ocufit device is retained in the lower fornix for 1 or 2 days only.

EXAMPLE 9

Experiments were carried out to study release kinetics of the present invention.

In FIGS. 14 to 17, there are provided various graphs showing drug release data for materials that can be used to form devices of the present invention. In these studies a Nusil Med-4830 elastomer was employed and the release rate for efficacy is shown as well as results obtained when the device was loaded with fluorescein disodium and various excipients.

The data in FIGS. 14 to 17 show release rate from the device made of a Nusil MED-4830 loaded only with fluorescein disodium as a drug representative and release rates from the devices loaded with excipients in addition to fluorescein.

Figure 17:
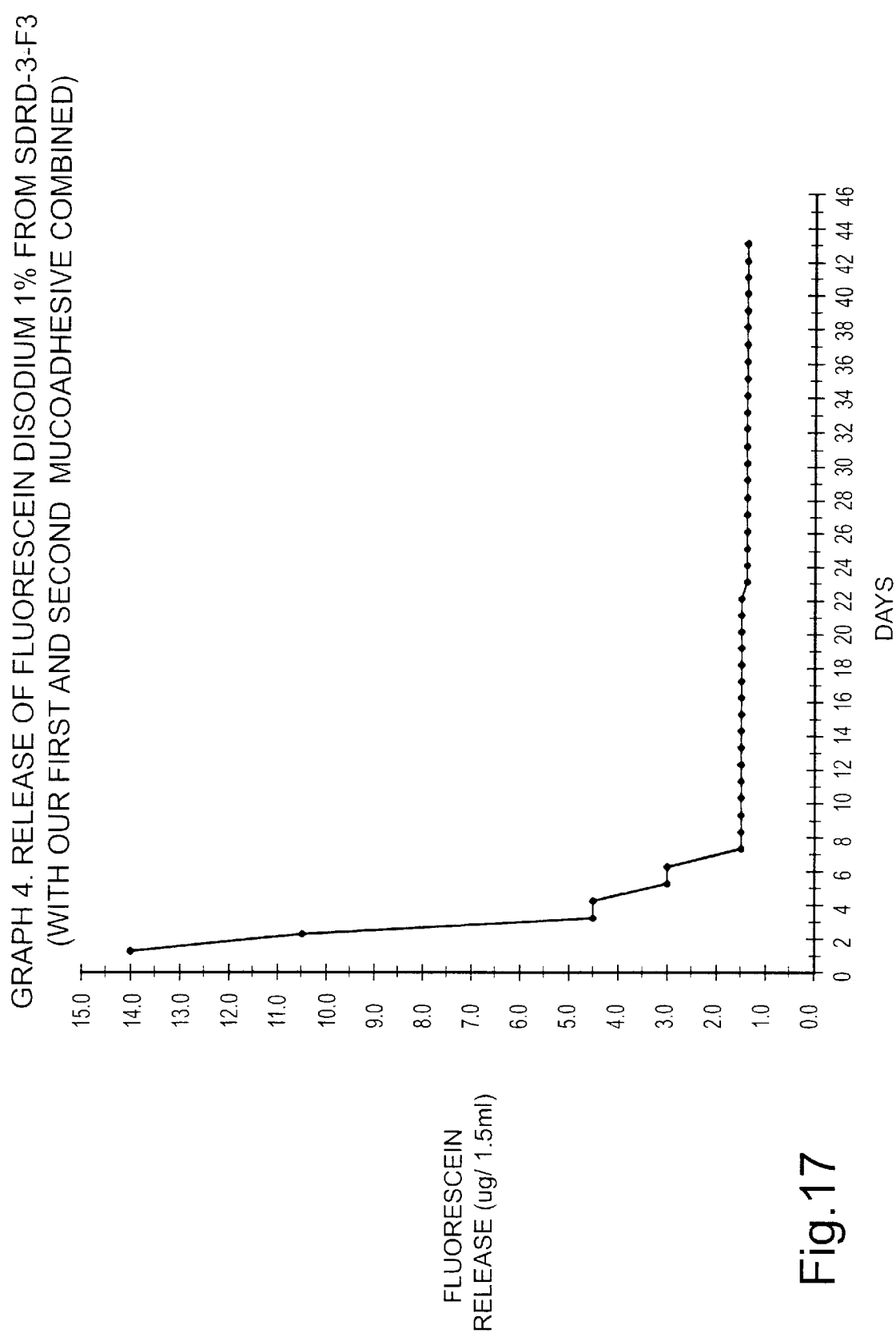

As shown in the graphs 15 and 16, devices loaded with Carbopol or hydroxypropylmethyl cellulose (HPMC) provided a highly desirable zero order or near zero order release kinetics. FIG. 17 shows a graph release data in accordance with the present invention, in which loading the device with Carbopol and HPMC combined provided a long term release kinetic of zero order or near zero order for over a month period.

EXAMPLE 10

In Table 6 and FIGS. 18 to 21 there are shown data graphs of the swelling rate of a particular elastomer employed in a device of the present invention. Swelling is caused by the migration of water into the polymer, dissolving the drug and causing the polymer to swell due to an osmotic effect as water forces the polymer outwardly. Such swelling can be desirable inasmuch as a device of the present invention may lock into place as it grows in size and facilitates diffusion of the drug. It has been found that when silicone materials are loaded with drugs and/or excipients they are particularly prone to swell in this manner. As indicated by the graphs, it is within the scope of the invention to select the initial dimensions of a device and, by selecting the proper combination of solid drugs and excipients, to provide for the desired final dimensions of the device after swelling.

FIG. 18 shows that silicone elastomer alone does not swell when exposed to water.

In FIGS. 19 to 21 there are shown the measurements obtained with regard to swelling of a device of the present invention which has been loaded with carbopol, HPMC or combined carbopol and HPMC. At large drug loads, the device can swell so that both length and diameter are increased significantly. In view of this tendency to swell when drugs and/or excipients have been incorporated, there are several possible approaches: (1) start with a small rod that is initially inserted; (2) adjust the ratio of drug to release modifiers which will affect the rate of water diffusion into the device; and (3) adjust the amount of platinum catalyst to facilitate more complete cross-linking of the polymeric material which reduces the amount of swelling.

The data in appended Table 6 show physical properties, including % elongation and swelling for a device of the present invention prepared in various formulations with various amounts of Carbopol, HPMC or combined Carbopol and HMPC, or various amounts of oxytetracycline and dextrose.

EXAMPLE 11

It is generally the case that antibacterial drugs are particularly effective against either the gram positive or gram negative group of bacteria. The present invention can provide simultaneous doses of drugs separately more active against each group so saving time and expense in determining which type of bacteria is present in the eye. The drugs may also be selected which also provide additive, synergistic or complementary effects when present together in the eye fluid.

EXAMPLE 12

The approaches to the treatment of glaucoma fall, generally, into two categories; improving drainage from the anterior chamber or reducing production of the aqueous humour. It may not be known which is the primary cause of the ailment in which case the present invention may be used to provide dosage of different drugs each treating the different possible cause simultaneously.

While the ocular insert of the present invention has been described herein as particularly well suited for treatment of humans, it is also within the scope of the invention to employ the present invention in the treatment of other animals such as cows and horses for diseases such as pink eye and the like.

The invention may be embodied in other specific forms without departing from the spirit or essential characteristics thereof. The present embodiments are therefore to be considered in all respects as illustrative and not restrictive. The scope of the invention being indicated by the appended claims rather than by the foregoing description, and all changes which come within the meaning and range of equivalency of the claims are therefore intended to be embraced therein.

TABLE 1

RETENTION OF SDRD-3
(NEW SHAPE MEASURING 20 × 1$^{MM}$)
IN THE UPPER FORNIX OF 25 ADULT VOLUNTEERS
WITH NORMAL EYES

| Days SDRD-3 retained | Number retained | |
| --- | --- | --- |
| | No. | % |
| More than 1 day | 22 | 88 |
| More than 2 days | 21 | 84 |
| More than 3 days | 20 | 80 |
| More than 5 days | 19 | 76 |
| More than 6 days | 18 | 72 |
| 28 days or more* | 28 | 72 |
| Total | 25 | 100 |

* = The insert was removed after 28 days

TABLE 2

CUMULATIVE RETENTION OF SDRD-3
(NEW SHAPE MEASURING 20 × 1$^{MM}$)
IN THE UPPER FORNIX OF 25 ADULT VOLUNTEERS
WITH NORMAL EYES.

| Weeks SDRD-3 retained | Number retained | |
|---|---|---|
| | No. | % |
| More than one week | 18 | 72 |
| More than two weeks | 18 | 72 |
| More than three weeks | 18 | 72 |
| Four weeks or more* | 18 | 72 |
| Total | 25 | 100 |

* = The insert was removed after 28 days

TABLE 5

CUMULATIVE RETENTION OF SDRD - 3
(NEW SHAPE MEASURING 20 × 1$^{MM}$)
IN THE LOWER FORNIX OF 25 ADULT VOLUNTEERS
WITH NORMAL EYES

| WEEKS SDRD-3 Retained | Number Retained | |
|---|---|---|
| | No | % |
| More than one week | 11 | 44 |
| More than two weeks | 11 | 44 |
| More than three weeks | 10 | 40 |
| Four weeks or more* | 9 | 36 |
| Total | 25 | 100 |

*The insert was removed after day 28

TABLE 3

COMPARATIVE RETENTION OF SDRD - 3
(NEW SHAPE MEASURING 20 × 1$^{MM}$)
AND OCUFIT - SR
IN THE UPPER FORNIX OF ADULT HUMAN EYES

| | | | No of | Duration and Number Retained (Weeks) | | | | | | | |
|---|---|---|---|---|---|---|---|---|---|---|---|
| | | Size | Eyes | >1 week | | >2 weeks | | >3 weeks | | ≧4 weeks | |
| Studies | Type of Insert | (mm) | Inserted | No | % | No | % | No | % | No | % |
| 1 Islamabad, Pakistan 1998* | SDRD-3 (Ribbed) | 20 × 1 | 25 | 18 | 72 | 18 | 72 | 18 | 72 | 18 | 72 |
| 2 Uppsala, Sweden 1995* | OCUFIT-SR (Ribbed) | 25 × 1.5 | 25 | 15 | 60 | 12 | 48 | 11 | 44 | 7 | 28 |
| 3 Karachi, Pakistan 1991* | OCUFIT-SR (Un-ribbed) | 25 × 1.5 | 17 | 12 | 71 | 9 | 53 | 8 | 47 | 8 | 47 |
| 4 London, England 1992* | OCUFIT - SR (Ribbed) | 25 × 1.5 | 9 | 6 | 67 | 5 | 56 | 5 | 56 | 4 | 44 |
| 5 Karachi, Pakistan 1992** | OCUFIT - SR (Un-ribbed) | 25 × 1.5 | 50 | 31 | 62 | 17 | 34 | 10 | 20 | 7 | 14 |
| 6 Karachi, Pakistan 1992** | OCUFIT - SR (Ribbed) | 25 × 1.5 | 24 | 15 | 62 | 9 | 37 | 8 | 33 | 7 | 29 |
| 7 Islamabad, Pakistan 1998* | OCUFIT-SR (Un-ribbed) | 2–12 × 1.5 | 30 | 10 | 33 | 10 | 33 | 10 | 33 | 9 | 30 |

*In volunteers with normal eyes
**In volunteers with an eye ailment (mainly infection)

TABLE 4

RETENTION OF SDRD - 3
(NEW SHAPE MEASURING 20 × 1$^{MM}$)
IN THE LOWER FORNIX OF 25 ADULT VOLUNTEERS
WITH NORMAL EYES

| Days SDRD-3 retained | Number Retained | |
|---|---|---|
| | No | % |
| More than 1 day | 23 | 92 |
| More than 2 days | 17 | 68 |
| More than 3 days | 13 | 52 |
| More than 5 days | 12 | 48 |
| More than 6 days | 11 | 44 |
| More than 20 days | 10 | 40 |
| More than 24 days | 9 | 36 |
| 28 days or more* | 9 | 36 |
| Total | 25 | 100 |

*The insert was removed after day 28

TABLE 6

| | Rate of swelling of the device | |
|---|---|---|
| Formulation | Length (%) | Diameter (%) |
| Silicone elastomer only | 0 | 0 |
| Silicone elastomer + 5% Carbopol | 0 | 0 |
| Silicone elastomer + 20% HPMC | 15 | 14 |
| Silicone elastomer + 5% Carbopol + 20% HPMC | 15 | 14 |
| Silicone elastomer + 15% Oxytetracyclin and 15% Dextrose | 15 | 28 |
| Silicone elastomer + 20% Oxytetracyclin and 20% Dextrose | 15 | 17 |

What is claimed is:

1. A flexible ocular insert device adapted for the controlled sustained release of a drug upon insertion into the upper or lower fornix of the eye, said device comprising an elongate body of a polymeric material including two end portions said body containing a pharmaceutically active ingredient, said device having a length of at least 8 mm and a maximum diameter not exceeding 1.9 mm, wherein said device is sufficiently flexible to allow it to bend along the curvature of the eye within the upper or lower fornix upon being positioned so that the longitudinal axis of said device is generally parallel to the transverse diameter of the eyeball, the device does not extend onto any visible portion of the eyeball, and in which each of said end portions is tapered towards the extremities of the device.

2. A device according to claim 1, in which the end portions are each in the form of a right circular cone.

3. A device according to claim 1, in which the end portions are each in the form of an oblique circular cone.

4. A device according to claim 1 in which the apex of each end portion is rounded.

5. A device according to claim 1, wherein the length of the device is from 8 to 25 mm for use in the lower fornix to suit the eyes of different sizes such as infants, children and adults.

6. A device according to claim 1, wherein the length of the device is from 8 to 35 mm for use in the upper fornix to suit the eyes of different sizes such as infants, children and adults.

7. A device according to claim 6, wherein the diameter of the device is from 0.5 to 1.9 mm to suit the eyes of different sizes such as infants, children and adults.

8. A device according to claim 1, wherein the body is tubular and the mechanism of drug release is by diffusion through an outer wall of the device.

9. A device according to claim 1, wherein the mechanism of drug release is by osmosis.

10. A device according to claim 1, wherein the mechanism of drug release is bioerosion.

11. A device according to claim 1, wherein the mechanism of drug release is by diffusion including possible drug dissolution.

12. A device according to claim 1, wherein the polymeric material is a silicone elastomer.

13. A device according to claim 1, wherein the polymeric material is made of hydrogel components.

14. A device according to claim 1, wherein the polymeric material is a methacrylate or hydroxymethacrylate based material.

15. A device adapted for the controlled sustained release of two or more drugs upon insertion into the upper or lower fornix of the eye, said device comprising an elongated body of a polymeric material including two end portions said body containing pharmaceutically active ingredient, said device having a length of at least 8 mm and a maximum diameter not exceeding 1.9 mm, wherein said device is sufficiently flexible to allow it to bend along the curvature of the eye within the upper or lower fornix upon being positioned so that the longitudinal axis of said device is generally parallel to the transverse diameter of the eyeball, and which at least two distinct portions of the device include respective distinct ones of said drugs.

16. A flexible insert device as claimed in claim 15 and in which said end portions are tapered towards respective extremities of the device.

17. A device according to claim 16, in which the end portions are each in the form of a right circular cone.

18. A device according to claim 16, in which the end portions are each in the form of an oblique circular cone.

19. A device according to claim 16 in which the apex of each end portion is rounded.

20. A device according to claim 16, wherein the length of the device is from 8 to 25 mm for use in the lower fornix to suit the eyes of different sizes such as infants, children and adults.

21. A device according to claim 16, wherein the length of the device is from 8 to 35 mm for use in the upper fornix to suit the eyes of different sizes such as infants, children and adults.

22. A device according to claim 16, wherein the diameter of the device is from 0.5 to 1.9 mm to suit the eyes of different sizes such as infants, children and adults.

23. A device according to claim 16, wherein the body is tubular and the mechanism of drug release is by diffusion through an outer wall of the device.

24. A device according to claim 16, wherein the mechanism of drug release is by osmosis.

25. A device according to claim 16, wherein the mechanism of drug release is bioerosion.

26. A device according to claim 16, wherein the mechanism of drug release is by diffusion including possible drug dissolution.

27. A device according to claim 16, wherein the polymeric material is a silicone elastomer.

28. A device according to claim 16, wherein the polymeric material is made of hydrogel components.

29. A device according to claim 16, wherein the polymeric material is a methacrylate or hydroxymethacrylate based material.

30. A method for the controlled sustained release of one or more drugs into the eye over a period of time comprising inserting a flexible ocular insert device according to claim 1 or 15 into position in the upper or lower fornix of the eye and allowing said device to remain in the fornix for drug release during said period of time.

31. A device according to claim 7 incorporating one or more radial protrusions, wherein the diameter of the device including said protrusions is from 0.5 to 1.9 mm to suit the eyes of different sizes such as infants, children and adults.

32. A device according to claim 22 incorporating one or more radial protrusions, wherein the diameter of the device including said protrusions is from 0.5 to 1.9 mm to suit the eyes of different sizes such as infants, children and adults.

* * * * *